US 12,140,589 B2

(12) United States Patent
Abe

(10) Patent No.: US 12,140,589 B2
(45) Date of Patent: Nov. 12, 2024

(54) GAS DETECTION SYSTEM

(71) Applicant: KYOCERA Corporation, Kyoto (JP)

(72) Inventor: Shinichi Abe, Uji (JP)

(73) Assignee: KYOCERA CORPORATION, Kyoto (JP)

(*) Notice: Subject to any disclaimer, the term of this patent is extended or adjusted under 35 U.S.C. 154(b) by 387 days.

(21) Appl. No.: 17/605,536

(22) PCT Filed: Apr. 20, 2020

(86) PCT No.: PCT/JP2020/017089
§ 371 (c)(1),
(2) Date: Oct. 21, 2021

(87) PCT Pub. No.: WO2020/218255
PCT Pub. Date: Oct. 29, 2020

(65) Prior Publication Data
US 2022/0196633 A1 Jun. 23, 2022

(30) Foreign Application Priority Data
Apr. 24, 2019 (JP) ................. 2019-083066

(51) Int. Cl.
G01N 33/00 (2006.01)
G01N 33/497 (2006.01)

(52) U.S. Cl.
CPC ....... G01N 33/497 (2013.01); G01N 33/0073 (2013.01)

(58) Field of Classification Search
CPC .... G01N 33/497; G01N 33/0073; G01N 1/00; G01N 27/12; G01N 33/0014; G01N 33/0026; G01N 33/0029; G01F 23/34

USPC ... 73/1.06, 1.07, 23.2, 23.42, 23.41, 863.72, 73/863.73, 864.21, 864.84; 422/88, 89
See application file for complete search history.

(56) References Cited

U.S. PATENT DOCUMENTS

| 5,239,492 | A | * | 8/1993 | Hartwig | ............. G01N 33/0006 73/1.07 |
| 6,672,129 | B1 | * | 1/2004 | Frederickson | ...... A61M 15/025 73/1.06 |
| 2017/0089875 | A1 | | 3/2017 | Hasegawa et al. | |
| 2020/0173967 | A1 | | 6/2020 | Abe | |

FOREIGN PATENT DOCUMENTS

| CA | 2221280 | * | 1/1997 |
| EP | 1746158 | * | 1/2007 |
| JP | 2017-67538 A | | 4/2017 |

(Continued)

Primary Examiner — Robert R Raevis
(74) Attorney, Agent, or Firm — Procopio, Cory, Hargreaves & Savitch LLP

(57) ABSTRACT

A gas detection system includes a sensor unit that outputs a voltage corresponding to a concentration of a specific gas, a first chamber capable of storing a supplied sample gas, a second chamber located between the first chamber and the sensor unit, and a flow path connectable to an inlet of the second chamber. The second chamber has a smaller area than the first chamber in a cross section perpendicular to a gas flow direction in the first chamber. The sample gas is supplied from the first chamber to the second chamber, and then a purge gas is supplied from the flow path to the second chamber to supply the sample gas to the sensor unit.

8 Claims, 16 Drawing Sheets

(56) References Cited

FOREIGN PATENT DOCUMENTS

WO 2019/022081 * 1/2019
WO 2019/022081 A1 1/2019
WO 2019244613 * 12/2019

* cited by examiner

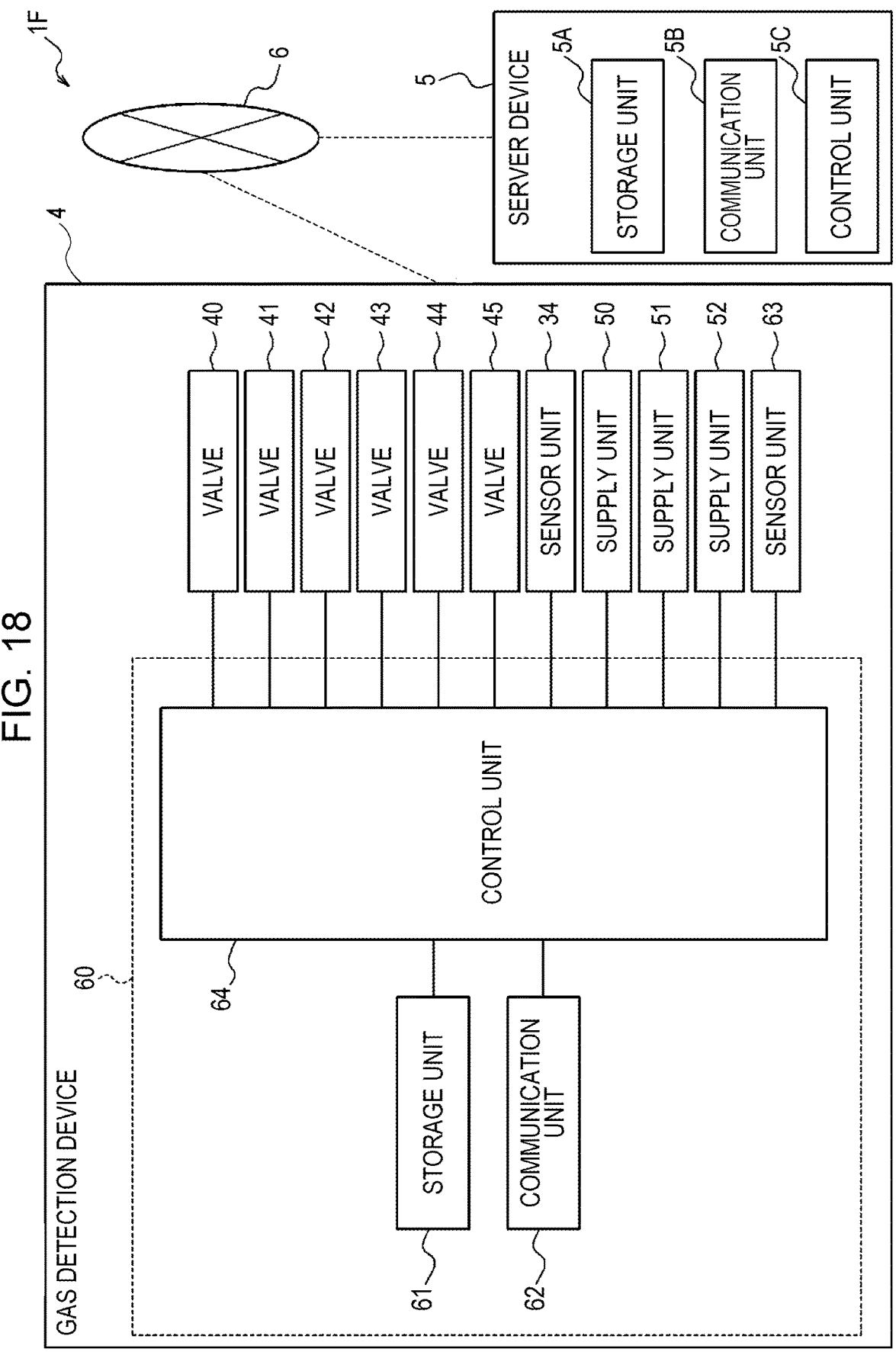

GAS DETECTION SYSTEM

CROSS REFERENCE TO RELATED APPLICATIONS

The present application claims priority to Japanese Patent Application No. 2019-083066 filed in Japan on Apr. 24, 2019, the entire disclosure of which is incorporated herein by reference.

TECHNICAL FIELD

The present disclosure relates to a gas detection system.

BACKGROUND ART

In the related art, there is known a system for detecting an odoriferous gas generated from feces discharged by a subject (for example, PTL 1).

CITATION LIST

Patent Literature

PTL 1: Japanese Unexamined Patent Application Publication No. 2017-67538

SUMMARY OF INVENTION

A gas detection system according to an embodiment of the present disclosure includes:
 a sensor unit that outputs a voltage corresponding to a concentration of a specific gas;
 a first chamber capable of storing a supplied sample gas;
 a second chamber located between the first chamber and the sensor unit; and
 a flow path connectable to an inlet of the second chamber, wherein
 the second chamber has a smaller area than the first chamber in a cross section perpendicular to a gas flow direction in the first chamber, and
 the sample gas is supplied from the first chamber to the second chamber, and then a purge gas is supplied from the flow path to the second chamber to supply the sample gas to the sensor unit.

A gas detection system according to an embodiment of the present disclosure includes:
 a sensor unit that outputs a voltage corresponding to a concentration of a specific gas; and
 a control unit capable of controlling flow rates of a sample gas and a purge gas to be supplied to the sensor unit, wherein
 when supplying the sample gas to the sensor unit, the control unit reduces a flow rate of the sample gas after a lapse of a first time from a start of supply of the sample gas to the sensor unit to smaller than a flow rate of the sample gas at the start of supply.

A gas detection system according to an embodiment of the present disclosure includes:
 a sensor unit that outputs a voltage corresponding to a concentration of a specific gas; and
 a control unit capable of controlling flow rates of a sample gas and a purge gas to be supplied to the sensor unit, wherein
 when supplying the sample gas to the sensor unit, after a lapse of a first time from a start of supply of the sample gas to the sensor unit, the control unit stops the supply of the sample gas to the sensor unit.

BRIEF DESCRIPTION OF DRAWINGS

FIG. 18 is a functional block diagram of a gas detection system according to another embodiment of the present disclosure.

DESCRIPTION OF EMBODIMENTS

Conventional systems are susceptible to improvement.

The present disclosure relates to providing an improved gas detection system.

According to an embodiment of the present disclosure, an improved gas detection system can be provided.

An embodiment according to the present disclosure will be described hereinafter with reference to the drawings schematically illustrating the embodiment.

[Example Configuration of Gas Detection System]

Figure 1:
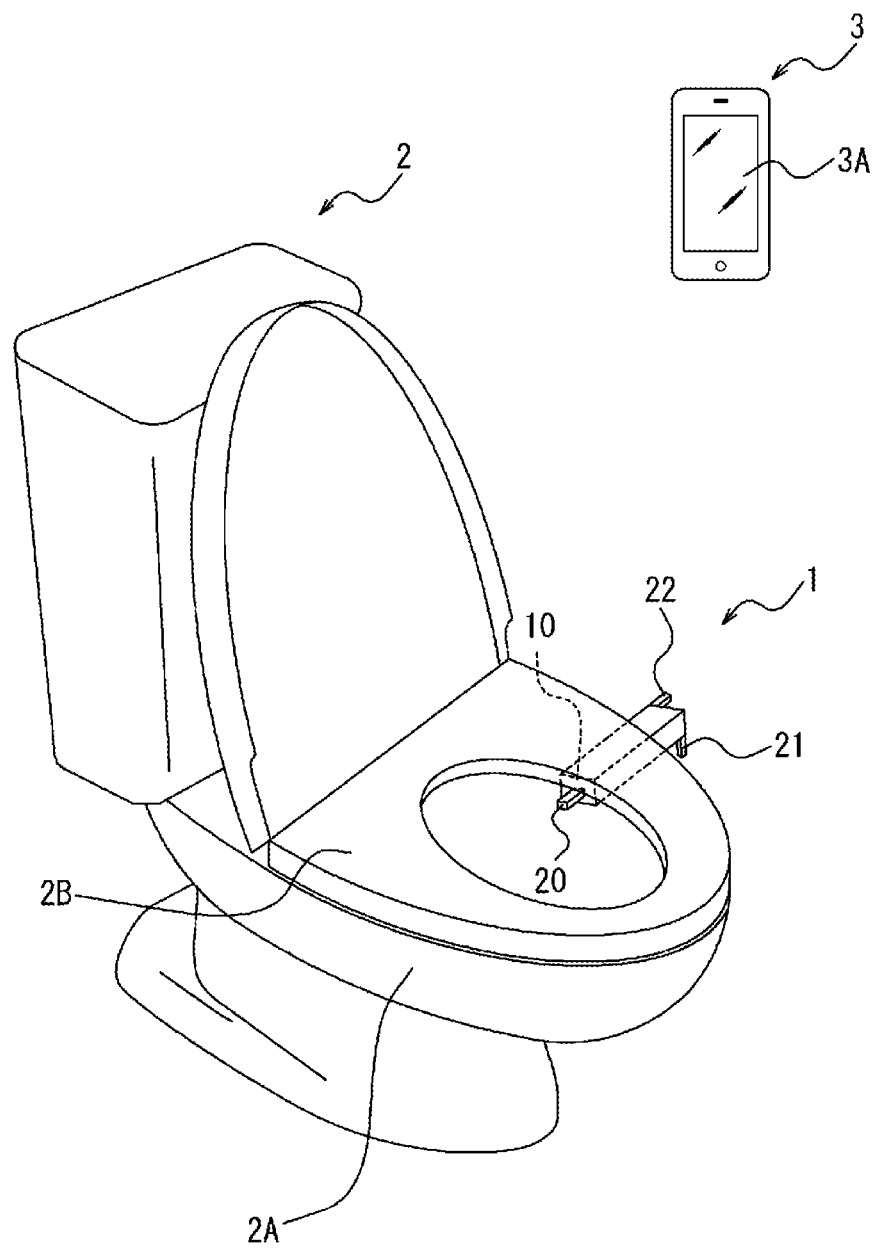
FIG. 1 is an external view of a gas detection system according to an embodiment of the present disclosure.

As illustrated in FIG. 1, the gas detection system 1 is installed in a toilet 2. The toilet 2 may be, but is not limited to, a flush toilet. The gas detection system 1 may be installed in any portion of the toilet 2. The toilet 2 includes a toilet bowl 2A and a toilet seat 2B. In one example, as illustrated in FIG. 1, the gas detection system 1 may be arranged from between the toilet bowl 2A and the toilet seat 2B to the outside of the toilet 2. A portion of the gas detection system 1 may be embedded inside the toilet seat 2B. A subject can discharge feces into the toilet bowl 2A of the toilet 2. The gas detection system 1 can acquire a gas generated from the feces discharged into the toilet bowl 2A as a sample gas. The gas detection system 1 can detect the type of a gas contained in the sample gas, the concentration of the gas, and so on.

The gas detection system 1 can transmit the detection results and so on to an electronic device 3. A gas detection system 1 as illustrated in FIG. 1 is also referred to as a "gas detection device".

The uses of the gas detection system 1 are not limited to the use described above. For example, the gas detection system 1 may be installed in a refrigerator. In this case, the gas detection system 1 can acquire a gas generated from food as a sample gas. In another use, for example, the gas detection system 1 may be installed in a factory or a laboratory. In this case, the gas detection system 1 can acquire a gas generated from a chemical or the like as a sample gas.

The toilet 2 can be installed in a toilet room in a house, a hospital, or the like. The toilet 2 can be used by the subject. As described above, the toilet 2 includes the toilet bowl 2A and the toilet seat 2B. The subject can discharge feces into the toilet bowl 2A.

The electronic device 3 is, for example, a smartphone used by the subject. However, the electronic device 3 is not limited to the smartphone and may be any electronic device. When brought into the toilet room by the subject, as illustrated in FIG. 1, the electronic device 3 can be present in the toilet room. However, for example, when the subject does not bring the electronic device 3 into the toilet room, the electronic device 3 may be present outside the toilet room. The electronic device 3 can receive the detection results from the gas detection system 1 via wireless communication or wired communication. The electronic device 3 can display the received detection results on a display unit 3A. The display unit 3A may include a display capable of displaying characters and the like, and a touch screen capable of detecting contact of a finger of the user (subject) or the like. The display may include a display device such as a liquid crystal display (LCD), an organic EL display (OELD: Organic Electro-Luminescence Display), or an inorganic EL display (IELD: Inorganic Electro-Luminescence Display). The detection method of the touch screen may be any method such as a capacitance method, a resistance film method, a surface acoustic wave method, an ultrasonic method, an infrared method, an electromagnetic induction method, or a load detection method.

Figure 2:
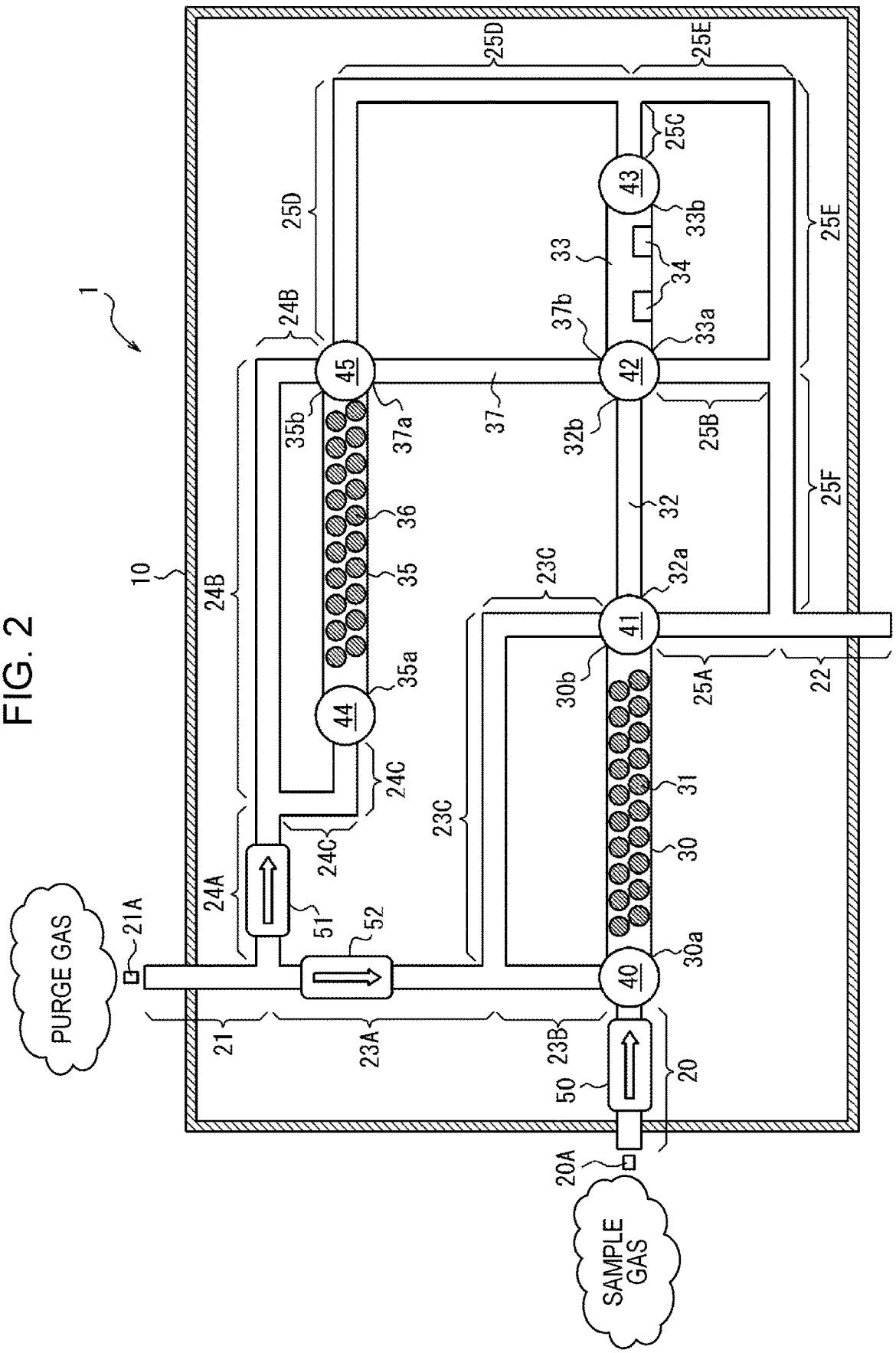
FIG. 2 is a schematic diagram of the inside of a housing of the gas detection system illustrated in FIG. 1.
Figure 3:
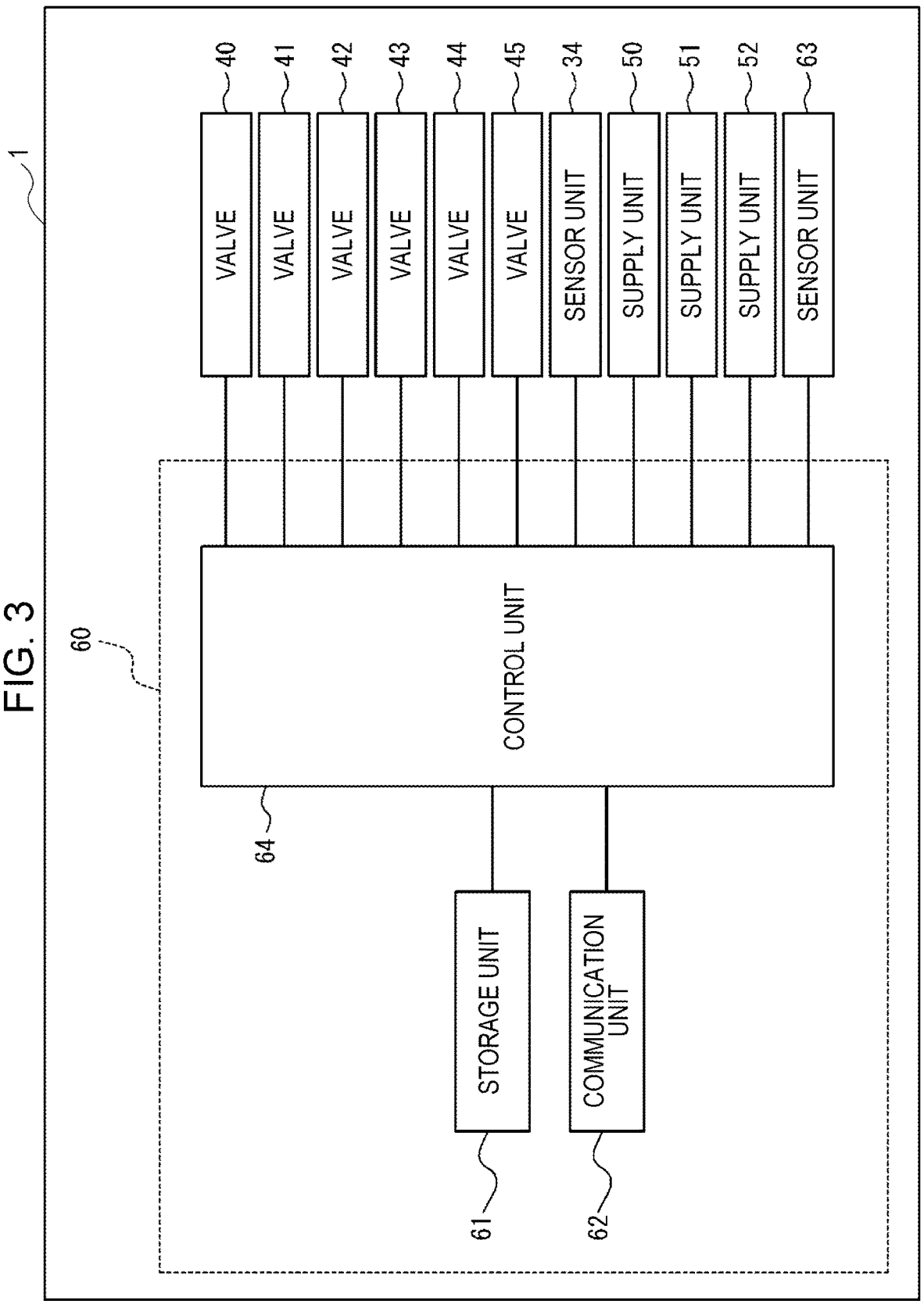
FIG. 3 is a functional block diagram of the gas detection system illustrated in FIG. 1.

As illustrated in FIG. 2, the gas detection system 1 includes a housing 10, a suction hole 20, a suction hole 21, a discharge path 22, and flow paths 23A, 23B, 23C, 24A, 24B, 24C, 25A, 25B, 25C, 25D, 25E, and 25F. The gas detection system 1 includes a first chamber 30, a second chamber 32, a third chamber 33, a fourth chamber 35, a fifth chamber 37, valves 40, 41, 42, 43, 44, and 45, and supply units 50, 51, and 52. The gas detection system 1 includes a plurality of sensor units 34 in the third chamber 33. As illustrated in FIG. 3, the gas detection system 1 includes a circuit board 60. The gas detection system 1 includes, in the circuit board 60, a storage unit 61, a communication unit 62, and a control unit 64. The gas detection system 1 includes a sensor unit 63. The gas detection system 1 may further include a battery, a speaker, and the like.

The housing 10 houses various components of the gas detection system 1. The housing 10 may be made of any material. For example, the housing 10 may be made of a material such as metal or resin.

As illustrated in FIG. 1, the suction hole 20 can be exposed to the inside of the toilet bowl 2A. A portion of the suction hole 20 may be embedded in the toilet seat 2B. The suction hole 20 sucks in a gas generated from feces discharged into the toilet bowl 2A as a sample gas. The sample gas sucked in through the suction hole 20 is supplied to and stored in the first chamber 30. As illustrated in FIG. 1, one end of the suction hole 20 may be directed to the inside of the toilet bowl 2A. As illustrated in FIG. 2, the other end of the suction hole 20 may be connected to the first chamber 30. The suction hole 20 may be constituted by a tubular member such as a resin tube or a metal or glass pipe.

As illustrated in FIG. 2, the suction hole 20 may have, on the outside thereof, an air blower 20A. The air blower 20A may include a fan and a motor. The air blower 20A can drive the motor to rotate the fan under the control of the control unit 64. The air blower 20A rotates the fan to draw a gas generated from feces into around the suction hole 20. The air blower 20A draws a gas generated from feces into around the suction hole 20, and the supply unit 50 is driven to allow the suction hole 20 to suck in the gas generated from the feces in the toilet bowl 2A.

As illustrated in FIG. 1, the suction hole 21 can be exposed to the outside of the toilet bowl 2A. A portion of the suction hole 21 may be embedded in the toilet seat 2B. The suction hole 21 sucks in, for example, air (surrounding gas) in the toilet room outside the toilet bowl 2A as a purge gas. The purge gas sucked in through the suction hole 21 is supplied to and stored in the fourth chamber 35 via the flow paths 24A and 24C. The purge gas sucked in through the suction hole 21 is also supplied to and stored in the first chamber 30 via the flow paths 23A and 23B. As illustrated in FIG. 1, one end of the suction hole 21 may be directed to the outside of the toilet 2. As illustrated in FIG. 2, the other end of the suction hole 21 may be connected to one end of the flow path 23A and one end of the flow path 24A. The suction hole 21 may be constituted by a tubular member such as a resin tube or a metal or glass pipe.

As illustrated in FIG. 2, the suction hole 21 may have, on the outside thereof, an air blower 21A. The air blower 21A may include a fan and a motor. The air blower 21A can drive the motor to rotate the fan under the control of the control unit 64. The air blower 21A rotates the fan to draw the air in the toilet room into around the suction hole 21. The air blower 21A draws the air in the toilet room into around the suction hole 21, and any one of the supply unit 51 and the supply unit 52 is driven to allow the suction hole 21 to suck in the air in the toilet room as a purge gas.

The discharge path 22 as illustrated in FIG. 2 discharges the exhaust from the first chamber 30 to the outside via the flow path 25A. The discharge path 22 discharges the exhaust from the second chamber 32 to the outside via the flow paths 25B and 25F. The discharge path 22 discharges the exhaust from the third chamber 33 to the outside via the flow paths 25E and 25F. The discharge path 22 discharges the exhaust from the fourth chamber 35 to the outside via the flow paths 25D, 25E, and 25F. As illustrated in FIG. 1, one end of the discharge path 22 is exposed from the toilet seat 2B. As illustrated in FIG. 2, the other end of the discharge path 22 is connected to one end of the flow path 25A and one end of the flow path 25F. The discharge path 22 may be constituted by a tubular member such as a resin tube or a metal or glass pipe.

As illustrated in FIG. 2, one end of the flow path 23A is connected to the suction hole 21 and one end of the flow path 24A. The other end of the flow path 23A is connected to one end of the flow path 23B and one end of the flow path 23C. One end of the flow path 23B is connected to one end of the flow path 23A and one end of the flow path 23C. The other end of the flow path 23B is connected to a connection port of the valve 40. One end of the flow path 23C is connected to one end of the flow path 23A and one end of the flow path 23B. The other end of the flow path 23C is connected to a connection port of the valve 41. The flow paths 23A to 23C may be each constituted by a tubular member such as a resin tube or a metal or glass pipe.

As illustrated in FIG. 2, one end of the flow path 24A is connected to the suction hole 21 and one end of the flow path 23A. The other end of the flow path 24A is connected to one end of the flow path 24B and one end of the flow path 24C. One end of the flow path 24B is connected to one end of the flow path 24A and one end of the flow path 24C. The other end of the flow path 24B is connected to a connection port of the valve 45. One end of the flow path 24C is connected to one end of the flow path 24A and one end of the flow path 24B. The other end of the flow path 24C is connected to a connection port of the valve 44. The flow paths 24A to 24C may be each constituted by a tubular member such as a resin tube or a metal or glass pipe.

As illustrated in FIG. 2, one end of the flow path 25A is connected to a connection port of the valve 41. The other end of the flow path 25A is connected to the discharge path 22 and one end of the flow path 25F. One end of the flow path 25B is connected to a connection port of the valve 42. The other end of the flow path 25B is connected to one end of the flow path 25E and one end of the flow path 25F. One end of the flow path 25C is connected to a connection port of the valve 43. The other end of the flow path 25C is connected to one end of the flow path 25D and one end of the flow path 25E. One end of the flow path 25D is connected to a connection port of the valve 45. The other end of the flow path 25D is connected to one end of the flow path 25C and one end of the flow path 25E. One end of the flow path 25E is connected to one end of the flow path 25C and one end of the flow path 25D. The other end of the flow path 25E is connected to one end of the flow path 25B and one end of the flow path 25F. One end of the flow path 25F is connected to one end of the flow path 25B and one end of the flow path 25E. The other end of the flow path 25F is connected to one end of the flow path 25A and the discharge path 22. The flow paths 25A to 25C may be each constituted by a tubular member such as a resin tube or a metal or glass pipe.

The first chamber 30 as illustrated in FIG. 2 may be cylindrical. The first chamber 30 may be linear. The first chamber 30 includes an inlet 30a and an outlet 30b at both ends thereof. The first chamber 30 may be made of a material such as glass, metal, or resin.

Figure 4:
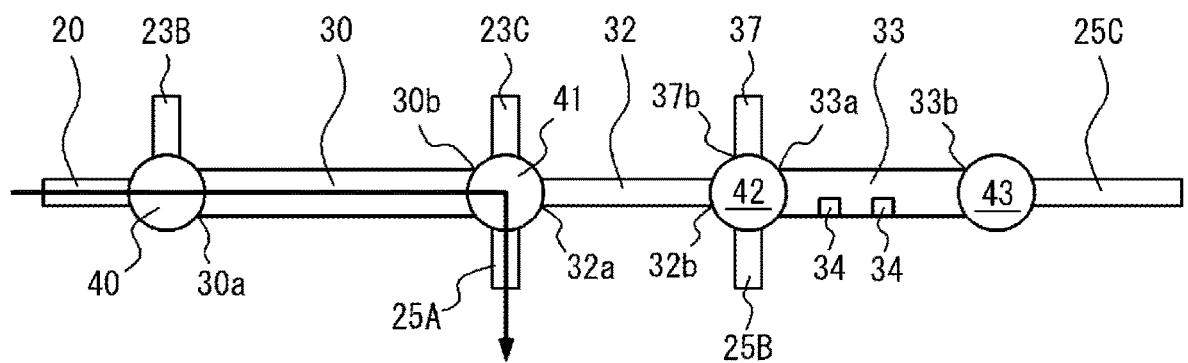
FIG. 4 is an explanatory view (part 1) illustrating a flow of gas in part of the configuration illustrated in FIG. 2.

The first chamber 30 as illustrated in FIG. 2 is supplied with a sample gas through the suction hole 20 (see FIG. 4). The first chamber 30 is capable of storing the supplied sample gas. The sample gas supplied to the first chamber 30 may be supplied to the second chamber 32 (see FIG. 5).

An adsorbent 31 may be placed in the first chamber 30. The adsorbent 31 may contain any material corresponding to the use. The adsorbent 31 may contain, for example, at least any one of activated carbon, silica gel, zeolite, and molecular sieve. The adsorbent 31 may be of a plurality of types or may contain a porous material.

The adsorbent 31 may adsorb a gas not to be detected contained in the sample gas. When the sample gas is a gas generated from feces, examples of the specific gas not to be detected include ammonia and water. Examples of the adsorbent 31 that adsorbs a gas not to be detected include silica gel and zeolite. Further, the sample gas may be concentrated in the first chamber 30. In this case, the adsorbent 31 may adsorb a gas to be detected contained in the sample gas. When the sample gas is a gas generated from feces, examples of the specific gas to be detected include methane, hydrogen, carbon dioxide, methyl mercaptan, hydrogen sulfide, acetic acid, and trimethylamine. Examples of the adsorbent 31 that adsorbs a gas to be detected include activated carbon and molecular sieve. However, the combination of them may be appropriately changed according to the polarity of gas molecules to be adsorbed.

Figure 5:
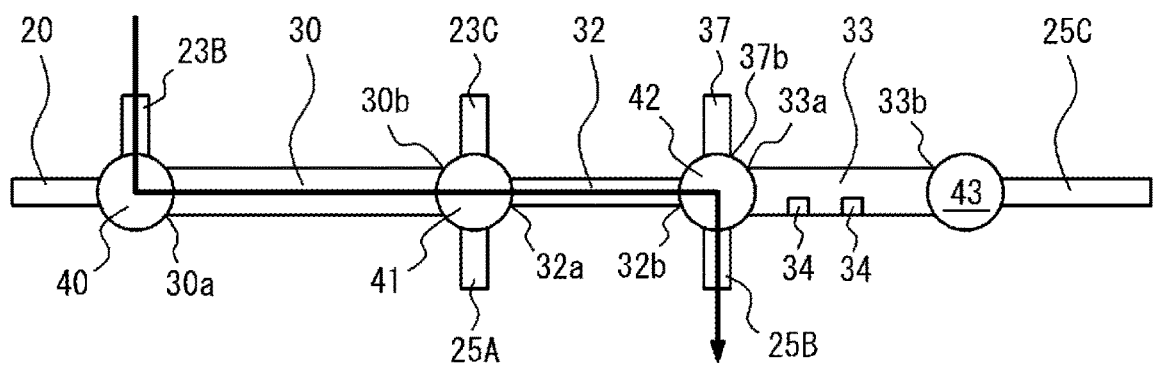
FIG. 5 is an explanatory view (part 2) illustrating a flow of gas in part of the configuration illustrated in FIG. 2.

As illustrated in FIG. 2, the second chamber 32 is located between the first chamber 30 and the third chamber 33. In other words, the second chamber 32 is located between the first chamber 30 and the sensor units 34. The second chamber 32 may be cylindrical. The second chamber 32 may be linear. The second chamber 32 includes an inlet 32a and an outlet 32b at both ends thereof. The second chamber 32 has a smaller area than the first chamber 30 in a cross section perpendicular to a gas flow direction in the first chamber 30. In the present disclosure, the term "gas flow direction in the first chamber 30" refers to a direction in which a gas flows from the first chamber 30 to the second chamber 32. For example, the gas flow direction in the first chamber 30 may be a direction in which, as illustrated in FIG. 5, the sample gas flows from the first chamber 30 toward the second chamber 32. In the present disclosure, the term "area of a chamber" refers not to the area of the chamber itself but to the area of a portion of the chamber that accommodates a gas. In a case where both the first chamber 30 and the second chamber 32 are cylindrical, the second chamber 32 may have a smaller cross-sectional area than the first chamber 30. The second chamber 32 may be made of a material such as glass, metal, or resin.

The second chamber 32 is supplied with the sample gas from the first chamber 30 and then supplied with a purge gas from the flow path 23C. The purge gas supplied from the flow path 23C to the second chamber 32 pushes out the sample gas in the second chamber 32 to the third chamber 33 (see FIG. 7). With this configuration, the sample gas in the second chamber 32 is supplied to the third chamber 33 and supplied to the sensor units 34.

The second chamber 32 may have a volumetric capacity smaller than or equal to the first chamber 30 and larger than the third chamber 33 in which the sensor units 34 are arranged. Setting the volumetric capacity of the second chamber 32 to be smaller than or equal to the volumetric capacity of the first chamber 30 can reduce the degree to which the sample gas is diluted with the purge gas in the first chamber 30. Further, since the volumetric capacity of the second chamber 32 is larger than the volumetric capacity of the third chamber 33, the sample gas in the second chamber 32 can be supplied to the third chamber 33 at least once or a plurality of times.

As illustrated in FIG. 2, the third chamber 33 is located between the second chamber 32 and the flow path 25C. The third chamber 33 is cylindrical. The third chamber 33 may be linear. The third chamber 33 includes an inlet 33a and an outlet 33b at both ends thereof. The third chamber 33 has the sensor units 34 arranged therein. The third chamber 33 may be made of a material such as glass, metal, or resin.

Figure 6:
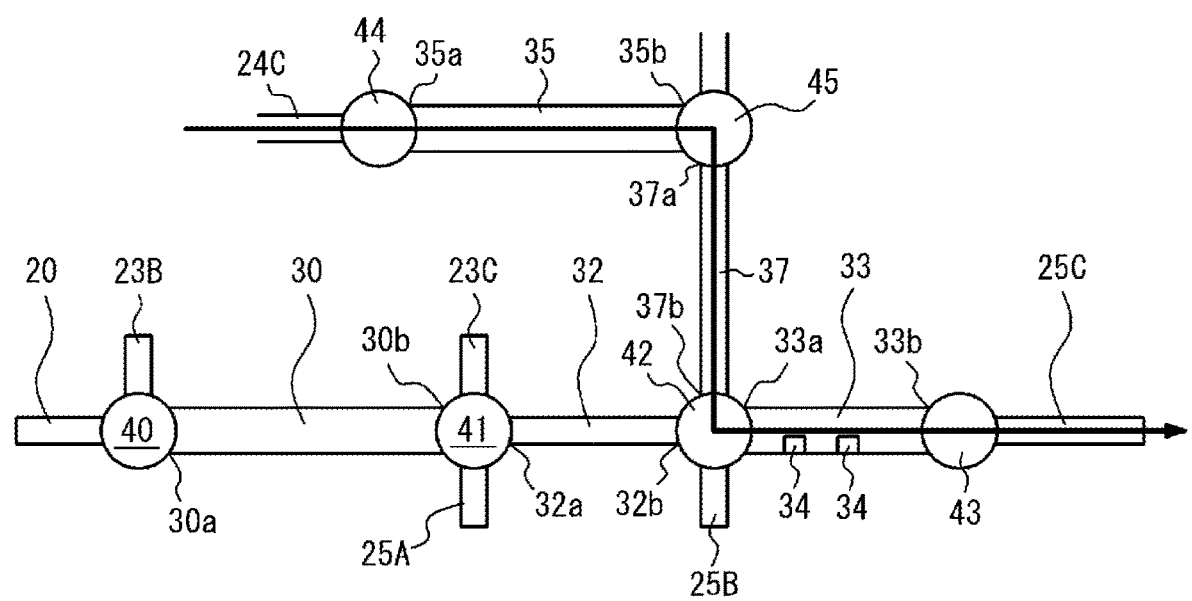
FIG. 6 is an explanatory view (part 3) illustrating a flow of gas in part of the configuration illustrated in FIG. 2.

The third chamber 33 is supplied with the purge gas from the fifth chamber 37 (see FIG. 6). The third chamber 33 is supplied with the sample gas from the second chamber 32 (see FIG. 7). The purge gas and the sample gas supplied to the third chamber 33 are supplied to the sensor units 34 and then discharged from the flow path 25C to the outside via the discharge path 22.

The sensor units 34 as illustrated in FIG. 2 are arranged in the third chamber 33. The sensor units 34 output voltages corresponding to the concentration of specific gases to the control unit 64. The specific gases contain a specific gas to be detected and a specific gas not to be detected. When the sample gas is a gas generated from feces, examples of the specific gas to be detected include methane, hydrogen, carbon dioxide, methyl mercaptan, hydrogen sulfide, acetic acid, and trimethylamine. When the sample gas is a gas generated from feces, examples of the specific gas not to be detected include ammonia and water. Each of the plurality of sensor units 34 can output a voltage corresponding to the concentration of at least any one of these gases to the control unit 64. Each of the sensor units 34 may include any one of a semiconductor sensor, a contact combustion sensor, an electrochemical sensor, or the like.

The fourth chamber 35 as illustrated in FIG. 2 is cylindrical. The fourth chamber 35 may be linear. The fourth chamber 35 includes an inlet 35*a* and an outlet 35*b* at both ends thereof. The fourth chamber 35 may be made of a material such as glass, metal, or resin.

The fourth chamber 35 is supplied with the purge gas via the flow path 24C. The fourth chamber 35 is capable of storing the supplied purge gas. The purge gas supplied to the fourth chamber 35 can be supplied to the fifth chamber 37.

An adsorbent 36 may be placed in the fourth chamber 35. The adsorbent 36 may contain any material corresponding to the use. The adsorbent 36 may contain, for example, at least any one of activated carbon, silica gel, zeolite, and molecular sieve. The adsorbent 36 may be of a plurality of types or may contain a porous material.

The adsorbent 36 may include an agent that adsorbs a gas not to be detected contained in the purge gas. Examples of the adsorbent 36 that adsorbs a gas not to be detected include silica gel and zeolite. The adsorbent 36 may include an agent that adsorbs a gas to be detected contained in the purge gas. Examples of the adsorbent 36 that adsorbs a gas to be detected include activated carbon and molecular sieve. However, the combination of them may be appropriately changed according to the polarity of gas molecules to be adsorbed. If the air in the toilet room is contaminated, the purge gas may contain a gas not to be detected and a gas to be detected. In this case, since the adsorbent 36 is placed in the fourth chamber 35, the contaminated air in the toilet room can be purified by the adsorbent 36. Since the air in the toilet room is purified by the adsorbent 36, a sufficient amount of purge gas can be maintained in the fourth chamber 35.

As illustrated in FIG. 2, the fifth chamber 37 is located between the third chamber 33 and the fourth chamber 35. The fifth chamber 37 is cylindrical. The fifth chamber 37 may be linear. The fifth chamber 37 includes an inlet 37*a* and an outlet 32*b* at both ends thereof. The fifth chamber 37 may be made of a material such as glass, metal, or resin.

As illustrated in FIG. 2, the valve 40 is located among the suction hole 20, the flow path 23B, and the inlet 30*a* of the first chamber 30. The valve 40 includes a connection port connected to the suction hole 20, a connection port connected to the flow path 23B, and a connection port connected to the inlet 30*a*. The valve 40 may be constituted by a valve such as an electromagnetically driven valve, a piezoelectrically driven valve, or a motor-driven valve.

The valve 40 switches the connection state among the suction hole 20, the flow path 23B, and the inlet 30*a* under the control of the control unit 64. For example, the valve 40 switches the connection state among them to a state in which the suction hole 20 and the inlet 30*a* are connected to each other, a state in which the flow path 23B and the inlet 30*a* are connected to each other, or a state in which the suction hole 20, the flow path 23B, and the inlet 30*a* are not connected to each other.

As illustrated in FIG. 2, the valve 41 is located among the flow path 23C, the flow path 25A, the outlet 30*b* of the first chamber 30, and the inlet 32*a* of the second chamber 32. The valve 41 includes a connection port connected to the flow path 23C, a connection port connected to the flow path 25A, a connection port connected to the outlet 30*b*, and a connection port connected to the inlet 32*a*. The valve 41 may be constituted by a valve such as an electromagnetically driven valve, a piezoelectrically driven valve, or a motor-driven valve.

The valve 41 switches the connection state among the flow path 23C, the flow path 25A, the outlet 30*b*, and the inlet 32*a* under the control of the control unit 64. For example, the valve 41 switches the connection state among them to a state in which the flow path 23C and the outlet 30*b* are connected to each other, a state in which the outlet 30*b* and the inlet 32*a* are connected to each other, or a state in which the flow path 23C and the inlet 32*a* are connected to each other. Alternatively, the valve 41 switches the connection state among them to a state in which the flow path 23C, the flow path 25A, the outlet 30*b*, and the inlet 32*a* are not connected to each other.

As illustrated in FIG. 2, the valve 42 is located among the flow path 25B, the outlet 32*b* of the second chamber 32, the inlet 33*a* of the third chamber 33, and the outlet 37*b* of the fifth chamber 37. The valve 42 includes a connection port connected to the flow path 25B, a connection port connected to the outlet 32*b*, a connection port connected to the inlet 33*a*, and a connection port connected to the outlet 37*b*. The valve 42 may be constituted by a valve such as an electromagnetically driven valve, a piezoelectrically driven valve, or a motor-driven valve.

The valve 42 switches the connection state among the flow path 25B, the outlet 32*b*, the inlet 33*a*, and the outlet 37*b* under the control of the control unit 64. For example, the valve 42 switches the connection state among them to a state in which the flow path 25B and the outlet 32*b* are connected to each other, a state in which the inlet 33*a* and the outlet 37*b* are connected to each other, or a state in which the outlet 32*b* and the inlet 33*a* are connected to each other. Alternatively, the valve 42 switches the connection state among them to a state in which the flow path 25B, the outlet 32*b*, the inlet 33*a*, and the outlet 37*b* are not connected to each other.

As illustrated in FIG. 2, the valve 43 is located between the flow path 25C and the outlet 33*b* of the third chamber 33. The valve 43 includes a connection port connected to the flow path 25C, and a connection port connected to the outlet 33*b*. The valve 43 may be constituted by a valve such as an electromagnetically driven valve, a piezoelectrically driven valve, or a motor-driven valve.

The valve 43 switches the connection state between the flow path 25C and the outlet 33*b* under the control of the control unit 64. For example, the valve 43 switches the connection state between the flow path 25C and the outlet 33*b* to a state in which the flow path 25C and the outlet 33*b* are connected to each other, or a state in which the flow path 25C and the outlet 33*b* are not connected to each other.

As illustrated in FIG. 2, the valve 44 is located between the flow path 24C and the inlet 35*a* of the fourth chamber 35. The valve 44 includes a connection port connected to the flow path 24C, and a connection port connected to the inlet 35*a*. The valve 44 may be constituted by a valve such as an electromagnetically driven valve, a piezoelectrically driven valve, or a motor-driven valve.

The valve 44 switches the connection state between the flow path 24C and the inlet 35*a* under the control of the control unit 64. For example, the valve 44 switches the connection state between the flow path 24C and the inlet 35*a* to a state in which the flow path 24C and the inlet 35*a* are connected to each other, or a state in which the flow path 24C and the inlet 35a are not connected to each other.

As illustrated in FIG. 2, the valve 45 is located among the flow path 24B, the flow path 25D, the outlet 35b of the fourth chamber 35, and the inlet 37a of the fifth chamber 37. The valve 45 includes a connection port connected to the flow path 24B, a connection port connected to the flow path 25D, a connection port connected to the outlet 35b, and a connection port connected to the inlet 37a. The valve 45 may be constituted by a valve such as an electromagnetically driven valve, a piezoelectrically driven valve, or a motor-driven valve.

The valve 45 switches the connection state among the flow path 24B, the flow path 25D, the outlet 35b, and the inlet 37a under the control of the control unit 64. For example, the valve 45 switches the connection state among them to a state in which the outlet 35b and the inlet 37a are connected to each other, a state in which the flow path 25D and the outlet 35b are connected to each other, a state in which the flow path 24B and the inlet 37a are connected to each other, or a state in which the flow path 24B and the flow path 25D are connected to each other. Alternatively, the valve 45 switches the connection state among them to a state in which the flow path 24B, the flow path 25D, the outlet 35b, and the inlet 37a are not connected to each other.

The supply unit 50 as illustrated in FIG. 2 is attached to the suction hole 20. The supply unit 50 is capable of supplying the sample gas from the suction hole 20 to the first chamber 30 under the control of the control unit 64. The arrow illustrated in the supply unit 50 indicates the direction in which the supply unit 50 sends the sample gas. The supply unit 50 may be constituted by a piezoelectric pump, a motor pump, or the like.

The supply unit 51 as illustrated in FIG. 2 is attached to the flow path 24A. The supply unit 51 is capable of supplying the purge gas from the suction hole 21 to at least any one of the flow path 24B and the flow path 24C under the control of the control unit 64. The arrow illustrated in the supply unit 51 indicates the direction in which the supply unit 51 sends the purge gas. The supply unit 51 may be constituted by a piezoelectric pump or the like.

The supply unit 52 as illustrated in FIG. 2 is attached to the flow path 23A. The supply unit 52 is capable of supplying the purge gas from the suction hole 21 to at least any one of the flow path 23B and the flow path 23C under the control of the control unit 64. The arrow illustrated in the supply unit 52 indicates the direction in which the supply unit 52 sends the purge gas. The supply unit 52 may be constituted by a piezoelectric pump or the like.

The circuit board 60 as illustrated in FIG. 3 has mounted therein wiring through which an electrical signal propagates, the storage unit 61, the communication unit 62, the control unit 64, and the like.

The storage unit 61 as illustrated in FIG. 3 is constituted by, for example, a semiconductor memory, a magnetic memory, or the like. The storage unit 61 stores various kinds of information, a program for operating the gas detection system 1, and the like. The storage unit 61 may function as a work memory.

The communication unit 62 as illustrated in FIG. 3 is capable of communicating with the electronic device 3 as illustrated in FIG. 1. The communication unit 62 may be capable of communicating with an external server. The communication method used when the communication unit 62 communicates with the electronic device 3 and the external server may be a short-range wireless communication standard, a wireless communication standard for connecting to a mobile phone network, or a wired communication standard. The short-range wireless communication standard may include, for example, WiFi (registered trademark), Bluetooth (registered trademark), infrared, NFC (Near Field Communication), and the like. The wireless communication standard for connecting to a mobile phone network may include, for example, LTE (Long Term Evolution) or a fourth generation or higher mobile communication system, and the like. Alternatively, the communication method used when the communication unit 62 communicates with the electronic device 3 and the external server may be, for example, a communication standard such as LPWA (Low Power Wide Area) or LPWAN (Low Power Wide Area Network).

The sensor unit 63 as illustrated in FIG. 3 may include at least any one of an image camera, a personal identification switch, an infrared sensor, a pressure sensor, and the like. The sensor unit 63 outputs a detection result to the control unit 64.

For example, when the sensor unit 63 includes an infrared sensor, the sensor unit 63 detects reflected light from an object irradiated with infrared radiation from the infrared sensor, thereby being able to detect that the subject has entered the toilet room. The sensor unit 63 outputs, as a detection result, a signal indicating that the subject has entered the toilet room to the control unit 64.

For example, when the sensor unit 63 includes a pressure sensor, the sensor unit 63 detects a pressure applied to the toilet seat 2B as illustrated in FIG. 1, thereby being able to detect that the subject has sat on the toilet seat 2B. The sensor unit 63 outputs, as a detection result, a signal indicating that the subject has sat on the toilet seat 2B to the control unit 64.

For example, when the sensor unit 63 includes a pressure sensor, the sensor unit 63 detects a reduction in the pressure applied to the toilet seat 2B as illustrated in FIG. 1, thereby being able to detect that the subject has risen from the toilet seat 2B. The sensor unit 63 outputs, as a detection result, a signal indicating that the subject has risen from the toilet seat 2B to the control unit 64.

For example, when the sensor unit 63 includes an image camera, a personal identification switch, and the like, the sensor unit 63 collects data, such as a face image, the sitting height, and the weight. The sensor unit 63 identifies and detects a person from the collected data. The sensor unit 63 outputs, as a detection result, a signal indicating the identified person to the control unit 64.

For example, when the sensor unit 63 includes a personal identification switch and the like, the sensor unit 63 identifies (detects) a person in response to an operation of the personal identification switch. In this case, personal information may be registered (stored) in the storage unit 61 in advance. The sensor unit 63 outputs, as a detection result, a signal indicating the identified person to the control unit 64.

The control unit 64 as illustrated in FIG. 3 includes one or more processors. The one or more processors may include at least any one of a general-purpose processor that reads a specific program to execute a specific function, and a dedicated processor dedicated to a specific process. The dedicated processor may include an application specific IC (ASIC; Application Specific Integrated Circuit). The one or more processors may include a programmable logic device (PLD; Programmable Logic Device). The PLD may include an FPGA (Field-Programmable Gate Array). The control unit 64 may include at least any one of an SoC (System-on-a-Chip) and an SiP (System-in-a-Package) with which the one or more processors cooperate.

The control unit 64 performs control so that the air in the toilet room is sucked in through the suction hole 21 as illustrated in FIG. 2 as a purge gas. The control unit 64 performs control so that the purge gas sucked in through the suction hole 21 as illustrated in FIG. 2 is stored in the fourth chamber 35. For example, the control unit 64 causes the fan of the air blower 21A as illustrated in FIG. 2 to rotate to draw the purge gas into around the suction hole 21. Further, the control unit 64 causes the valve 44 to connect the flow path 24C and the inlet 35a of the fourth chamber 35 to each other, and causes the valve 45 to connect the outlet 35b of the fourth chamber 35 and the flow path 25D to each other. In addition, the control unit 64 controls the supply unit 51 to cause the suction hole 21 to suck in the purge gas drawn into around the suction hole 21 by the air blower 21A. The purge gas drawn into the suction hole 21 is supplied to and stored in the fourth chamber 35 via the flow paths 24A and 24C. The control unit 64 may cause the purge gas to be sucked in through the suction hole 21 after a predetermined time elapses after it is detected that the subject has risen from the toilet seat 2B on the basis of the detection result of the sensor unit 63.

When causing the purge gas to be sucked in through the suction hole 21, the control unit 64 may store the purge gas in the fourth chamber 35 if the cleanliness of the purge gas is high. For example, the control unit 64 may supply the purge gas to the sensor units 34 in the third chamber 33 and determine, based on the detection results of the sensor units 34, whether the cleanliness of the purge gas is high. If the control unit 64 determines that the degree of cleaning the purge gas is high, the control unit 64 may store the purge gas in the fourth chamber 35. In this case, the gas detection system 1 may further include a flow path that directly connects the suction hole 21 and the third chamber 33, and a discharge path that directly discharges the gas supplied to the third chamber 33 to the outside. The gas detection system 1 may further include, separately from the sensor units 34, a dedicated sensor unit that detects the cleanliness of the purge gas. The dedicated sensor unit may be disposed at the tip of the suction hole 21 as illustrated in FIG. 2 or between the suction hole 21 and the fourth chamber 35. In this case, the gas detection system 1 may further include a discharge path that directly discharges the gas supplied to the dedicated sensor unit to the outside.

The control unit 64 performs control so that the sample gas is sucked in through the suction hole 20 as illustrated in FIG. 2. For example, the control unit 64 causes the fan of the air blower 20A as illustrated in FIG. 2 to rotate to draw the sample gas into around the suction hole 20. The control unit 64 controls the supply unit 50 to cause the suction hole 20 to suck in the sample gas drawn into the suction hole 20. The control unit 64 may cause the sample gas to be sucked in through the suction hole 20 after a predetermined time elapses after it is detected that the subject has sat on the toilet seat 2B on the basis of the detection result of the sensor unit 63.

The control unit 64 performs control so that the sample gas sucked in through the suction hole 20 is stored in the first chamber 30. For example, the control unit 64 causes the valve 40 as illustrated in FIG. 4 to connect the suction hole 20 and the inlet 30a of the first chamber 30 to each other. Further, the control unit 64 causes the valve 41 as illustrated in FIG. 4 to connect the outlet 30b of the first chamber 30 and the flow path 25A to each other. The control unit 64 controls the supply unit 50 as illustrated in FIG. 2 to supply the sample gas from the suction hole 20 as illustrated in FIG. 2 to the first chamber 30, as illustrated in FIG. 4. The sample gas supplied from the suction hole 20 to the first chamber 30 through the inlet 30a pushes out the residual gas in the first chamber 30 toward the outlet 30b. The residual gas pushed out toward the outlet 30b is discharged to the outside from the flow path 25A via the discharge path 22 as illustrated in FIG. 2. With this configuration, as illustrated in FIG. 4, the sample gas is accumulated in the first chamber 30.

The control unit 64 performs control so that the sample gas stored in the first chamber 30 is supplied to the second chamber 32. For example, the control unit 64 causes the valve 40 as illustrated in FIG. 5 to connect the flow path 23B and the inlet 30a of the first chamber 30 to each other, and causes the valve 41 as illustrated in FIG. 5 to connect the outlet 30b of the first chamber 30 and the inlet 32a of the second chamber 32 to each other. Further, the control unit 64 causes the valve 42 as illustrated in FIG. 5 to connect the outlet 32b of the second chamber 32 and the flow path 25B to each other. In addition, the control unit 64 controls the supply unit 52 as illustrated in FIG. 2 to supply the purge gas from the suction hole 21 as illustrated in FIG. 2 to the first chamber 30 via the flow path 23B, as illustrated in FIG. 5. The purge gas supplied from the flow path 23B to the first chamber 30 through the inlet 30a pushes out the sample gas in the first chamber 30 toward the outlet 30b. The sample gas pushed out toward the outlet 30b is supplied to the second chamber 32 through the inlet 32a. The sample gas supplied to the second chamber 32 pushes out the residual gas in the second chamber 32 toward the outlet 32b. The residual gas pushed out toward the outlet 32b is discharged to the outside from the flow path 25B via the discharge path 22 as illustrated in FIG. 2. With this configuration, the sample gas stored in the first chamber 30 is supplied to the second chamber 32, as illustrated in FIG. 5.

The control unit 64 performs control so that the purge gas stored in the fourth chamber 35 is supplied to the sensor units 34 in the third chamber 33. For example, the control unit 64 causes the valve 44 as illustrated in FIG. 6 to connect the flow path 24D and the inlet 35a of the fourth chamber 35 to each other, and causes the valve 45 as illustrated in FIG. 6 to connect the outlet 35b of the fourth chamber 35 and the inlet 37a of the fifth chamber 37 to each other. Further, the control unit 64 causes the valve 42 as illustrated in FIG. 6 to connect the inlet 33a of the third chamber 33 and the outlet 37b of the fifth chamber 37 to each other, and causes the valve 43 as illustrated in FIG. 6 to connect the outlet 33b of the third chamber 33 and the flow path 25C to each other. In addition, the control unit 64 controls the supply unit 51 as illustrated in FIG. 2 to supply the purge gas from the suction hole 21 as illustrated in FIG. 2 to the fourth chamber 35, as illustrated in FIG. 6. The purge gas supplied to the fourth chamber 35 from the suction hole 21 pushes out the purge gas stored in the fourth chamber 35 to the fifth chamber 37. The purge gas pushed out to the fifth chamber 37 is supplied to the third chamber 33. The purge gas supplied from the fifth chamber 37 to the third chamber 33 through the inlet 33a is supplied to the sensor units 34 in the third chamber 33. When the purge gas is supplied to the sensor units 34, the sensor units 34 output voltages corresponding to specific gases contained in the purge gas to the control unit 64. The purge gas subjected to detection processing is discharged to the outside from the outlet 33b and the flow path 25C via the discharge path 22 as illustrated in FIG. 2.

Figure 7:
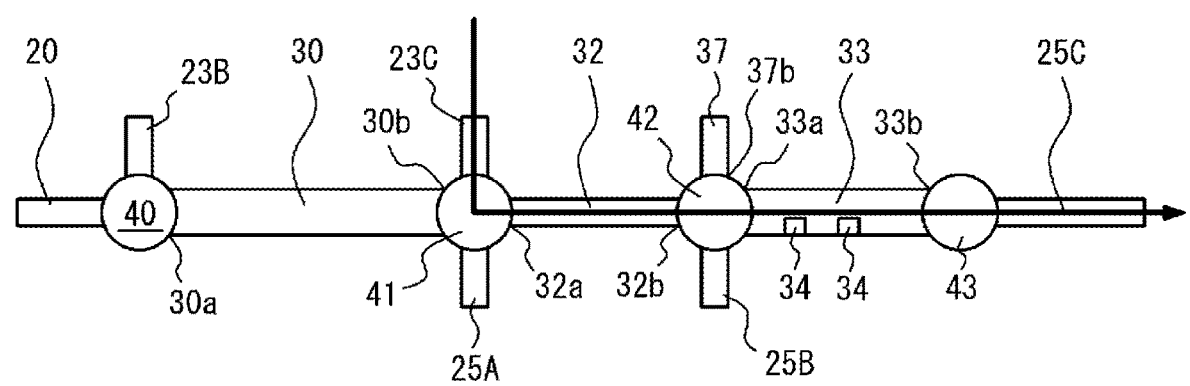
FIG. 7 is an explanatory view (part 4) illustrating a flow of gas in part of the configuration illustrated in FIG. 2.

The control unit 64 performs control so that the sample gas is supplied to the sensor units 34 in the third chamber 33. For example, the control unit 64 causes the valve 41 as illustrated in FIG. 7 to connect the flow path 23C and the inlet 32a of the second chamber 32 to each other, and causes the valve 42 as illustrated in FIG. 7 to connect the outlet 32*b* of the second chamber 32 and the inlet 33*a* of the third chamber 33 to each other. Further, the control unit 64 causes the valve 43 as illustrated in FIG. 7 to connect the outlet 33*b* of the third chamber 33 and the flow path 25C to each other. In addition, the control unit 64 controls the supply unit 52 as illustrated in FIG. 2 to supply the purge gas from the suction hole 21 as illustrated in FIG. 2 to the second chamber 32 from the flow path 23C, as illustrated in FIG. 7. The purge gas supplied from the flow path 23C to the second chamber 32 through the inlet 32*a* pushes out the sample gas in the second chamber 32 toward the outlet 32*b*. The sample gas pushed out toward the outlet 32*b* is supplied to the third chamber 33 from the inlet 33*a* through the outlet 32*b*. The sample gas supplied to the third chamber 33 is supplied to the sensor units 34. When the sample gas is supplied to the sensor units 34, the sensor units 34 output voltages corresponding to specific gases contained in the sample gas to the control unit 64. The sample gas subjected to detection processing is discharged to the outside from the outlet 33*b* and the flow path 25C via the discharge path 22 as illustrated in FIG. 2.

The control unit 64 alternately supplies the purge gas and the sample gas to the sensor units 34 in the third chamber 33 a predetermined number of times, for example. For example, the control unit 64 alternately repeats the control described with reference to FIG. 6 and the control described with reference to FIG. 7 a predetermined number of times, for example. The control unit 64 alternately supplies the purge gas and the sample gas to the third chamber 33 to acquire voltage waveforms from the sensor units 34. The control unit 64 detects the type and concentration of gases contained in the sample gas by, for example, machine learning for the voltage waveforms acquired from the sensor units 34. The control unit 64 may transmit the detected type and concentration of the gases to the electronic device 3 via the communication unit 62 as a detection result.

Figure 8:
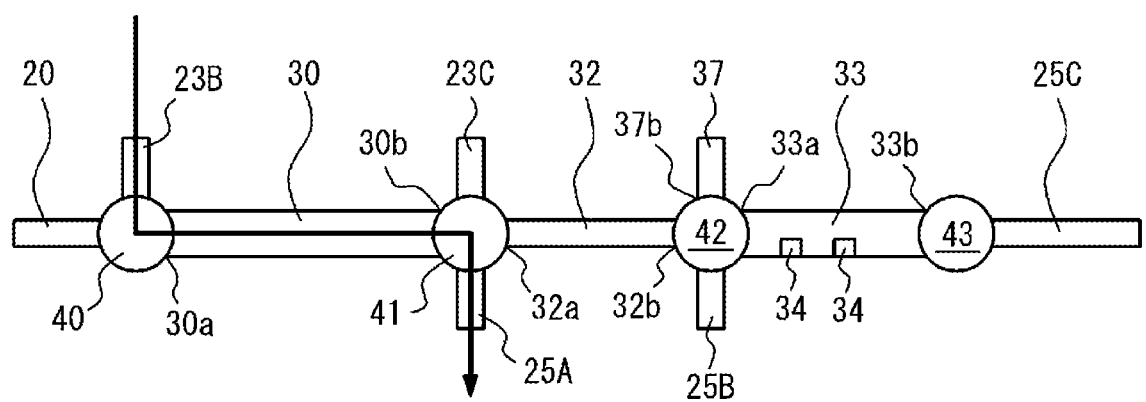
FIG. 8 is an explanatory view (part 5) illustrating a flow of gas in part of the configuration illustrated in FIG. 2.

For example, the control unit 64 performs control so that the sample gas remaining in the first chamber 30 is discharged from the first chamber 30 after detection processing. For example, the control unit 64 causes the valve 40 as illustrated in FIG. 8 to connect the flow path 23B and the inlet 30*a* of the first chamber 30 to each other, and causes the valve 41 as illustrated in FIG. 8 to connect the outlet 30*b* of the first chamber 30 and the flow path 25A to each other. Further, the control unit 64 controls the supply unit 52 as illustrated in FIG. 2 to supply the purge gas from the suction hole 21 as illustrated in FIG. 2 to the first chamber 30 from the flow path 23B, as illustrated in FIG. 8. The purge gas supplied from the flow path 23B to the first chamber 30 through the inlet 30*a* pushes out the sample gas remaining in the first chamber 30 toward the outlet 30*b*. The sample gas pushed out toward the outlet 30*b* is discharged to the outside from the flow path 25A via the discharge path 22 as illustrated in FIG. 2.

Here, the control unit 64 is capable of controlling the flow rate of the sample gas to be supplied to the third chamber 33. In other words, the control unit 64 is capable of controlling the flow rate of the sample gas to be supplied to the sensor units 34. For example, the control unit 64 controls the flow rate of the purge gas to be supplied from the flow path 23C as illustrated in FIG. 7 to the second chamber 32 by using the piezoelectric pump or motor pump of the supply unit 52 as illustrated in FIG. 2. The control unit 64 controls the flow rate of the purge gas to be supplied to the second chamber 32 as illustrated in FIG. 7, thereby controlling the flow rate of the sample gas to be pushed out to the third chamber 33 from the second chamber 32 by the purge gas. When supplying the sample gas to the third chamber 33 to supply the sample gas to the sensor units 34, the control unit 64 may appropriately control the flow rate of the sample gas.

The control unit 64 may perform control so that the flow rate of the sample gas at the start of supply to the sensor units 34 is larger than a first flow rate. The flow rate at the start of supply to the sensor units 34 may be appropriately determined in consideration of the influence on the output voltages of the sensor units 34 when the gas to be supplied to the sensor units 34 is switched from the purge gas to the sample gas. If the gas to be supplied to the sensor units 34 is switched from the purge gas to the sample gas or from the sample gas to the purge gas, the output voltages of the sensor units 34 can fall or rise and then become constant. The fall or rise of the output voltages of the sensor units 34 can be closer to that based on the reaction of the sensor units 34 themselves as the flow rate at the start of supply to the sensor units 34 increases. As the output voltages of the sensor units 34 are closer to that based on the reaction of the sensor units 34 themselves, the gas detection system 1 can more accurately detect the type and concentration of gases. That is, setting the flow rate of the sample gas at the start of supply to the sensor units 34 to be larger than the first flow rate allows the output voltages of the sensor units 34 to be closer to that based on the reaction of the sensor units 34 themselves. With this configuration, the gas detection system 1 can more accurately detect the type and concentration of gases.

The control unit 64 may perform control so that the flow rate of the sample gas, after the lapse of a first time from the start of supply of the sample gas to the sensor units 34, is smaller than the flow rate of the sample gas at the start of supply. Alternatively, after the lapse of the first time from the start of supply of the sample gas to the sensor units 34, the control unit 64 may stop the supply of the sample gas to the sensor units 34. For example, the control unit 64 may control the supply unit 52 as illustrated in FIG. 2 after the lapse of the first time, thereby performing control so that the flow rate of the purge gas to be supplied from the flow path 23C as illustrated in FIG. 7 to the second chamber 32 becomes smaller than the flow rate of the purge gas at the start of supply. Decreasing the flow rate of the purge gas to be supplied from the flow path 23C as illustrated in FIG. 7 to the second chamber 32 can decrease the flow rate of the sample gas to be pushed out to the third chamber 33 as illustrated in FIG. 7 from the second chamber 32 by the purge gas. Alternatively, the control unit 64 may control the supply unit 52 as illustrated in FIG. 2 after the lapse of the first time to stop the supply of the purge gas from the flow path 23C as illustrated in FIG. 7 to the second chamber 32. Stopping the supply of the purge gas from the flow path 23C as illustrated in FIG. 7 to the second chamber 32 can stop the supply of the sample gas from the second chamber 32 as illustrated in FIG. 7 to the third chamber 33. The sample gas is a gas generated from feces. Thus, the amount of sample gas that can be acquired may be limited. In particular, when the sample gas is concentrated, the amount of the sample gas is reduced. Even in this case, for example, the control unit 64 sets the flow rate of the sample gas after the lapse of the first time to be smaller than the flow rate of the sample gas at the start of supply. Thus, the control unit 64 can continuously supply the sample gas to the sensor units 34 for a longer period of time than when the flow rate of the sample gas is not reduced. With this configuration, the sensor units 34 can stably output voltages corresponding to specific gases contained in the sample gas. The first time may be appropriately set in consideration of the amount of sample gas that can be stored in the first chamber 30.

The control unit 64 may perform control so that a reduction in the flow rate of the sample gas and a stop of the supply of the sample gas to the sensor units 34 are alternately repeated after the lapse of the first time described above. In this case, the control unit 64 may perform control so that a reduction in the flow rate of the sample gas and a stop of the supply of the sample gas to the sensor units 34 are alternately repeated in accordance with the amount of the sample gas stored in the first chamber 30.

Here, the control unit 64 is capable of controlling the flow rate of the purge gas to be supplied to the third chamber 33. In other words, the control unit 64 is capable of controlling the flow rate of the purge gas to be supplied to the sensor units 34. For example, the control unit 64 controls the flow rate of the purge gas to be supplied from the fifth chamber 37 as illustrated in FIG. 6 to the third chamber 33 by using the piezoelectric pump of the supply unit 51 as illustrated in FIG. 2, thereby controlling the flow rate of the purge gas to be supplied to the third chamber 33. When supplying the purge gas to the sensor units 34 in the third chamber 33, the control unit 64 may appropriately control the flow rate of the purge gas.

The control unit 64 may perform control so that the flow rate of the purge gas at the start of supply to the sensor units 34 is larger than a second flow rate. The flow rate at the start of supply to the sensor units 34 may be appropriately determined in consideration of the influence on the output voltages of the sensor units 34 when the gas to be supplied to the sensor units 34 is switched, like the first flow rate described above. As described above, when the gas to be supplied to the sensor units 34 is switched, the output voltages of the sensor units 34 fall or rise. The fall or rise of the output voltages can be closer to that based on the reaction of the sensor units 34 themselves as the flow rate at the start of supply to the sensor units 34 increases. As described above, as the output voltages of the sensor units 34 are closer to that based on the reaction of the sensor units 34 themselves, the gas detection system 1 can more accurately detect the type and concentration of gases. That is, like the first flow rate described above, setting the flow rate of the purge gas at the start of supply to the sensor units 34 to be larger than the second flow rate allows the output voltages of the sensor units 34 to be closer to that based on the reaction of the sensor units 34 themselves. With this configuration, the gas detection system 1 can more accurately detect the type and concentration of gases.

The control unit 64 may perform control so that the flow rate of the purge gas, after the lapse of the second time from the start of supply of the purge gas to the sensor units 34, is smaller than or equal to the flow rate of the purge gas at the start of supply. Alternatively, the control unit 64 may stop the supply of the purge gas to the sensor units 34 after the lapse of the second time. For example, the control unit 64 may control the supply unit 51 as illustrated in FIG. 2 after the lapse of the second time, thereby performing control so that the flow rate of the purge gas to be supplied from the fifth chamber 37 as illustrated in FIG. 6 to the third chamber 33 becomes smaller than or equal to the flow rate of the purge gas at the start of supply. Alternatively, the control unit 64 may control the supply unit 51 as illustrated in FIG. 2 after the lapse of the second time to stop the supply of the purge gas from the fifth chamber 37 as illustrated in FIG. 7 to the third chamber 33. If the gas detection system 1 is installed in a toilet room, air in the toilet room may have been contaminated. In this case, the amount of purge gas that can be acquired may be limited. Even in this case, for example, the control unit 64 sets the flow rate of the purge gas after the lapse of the second time to be smaller than or equal to the flow rate of the purge gas at the start of supply. Thus, the control unit 64 can continuously supply the purge gas to the sensor units 34 for a longer period of time than when the flow rate of the purge gas is not reduced. With this configuration, the sensor units 34 can stably output voltages corresponding to specific gases contained in the purge gas. The second time may be appropriately set in consideration of the amount of purge gas that can be stored in the fourth chamber 35.

The control unit 64 may perform control so that the flow rate of the purge gas to be supplied to the sensor units 34 is larger than the flow rate of the sample gas to be supplied to the sensor units 34. For example, the control unit 64 may perform control so that the flow rate of the purge gas to be supplied from the fourth chamber 35 as illustrated in FIG. 6 to the third chamber 33 through the fifth chamber 37 is larger than the flow rate of the sample gas to be supplied from the second chamber 32 as illustrated in FIG. 7 to the third chamber 33. The sample gas generated from feces may be more limited in amount that can be acquired than the purge gas, which is the air in the toilet room. In particular, when the sample gas is concentrated, the amount of the sample gas is reduced. Further, increasing the flow rate of the purge gas allows a detection target gas adhering to the sensor units 34 by the purge gas to be more quickly removed from the sensor units 34. With this configuration, the gas detection system 1 can quickly remove the detection target gas adhering to the sensor units 34 from the sensor units 34 while saving the sample gas.

The control unit 64 may perform control so that the flow rate of the purge gas to be supplied to the first chamber 30 via the flow path 23B as illustrated in FIG. 5 is larger than the flow rate of the purge gas to be supplied from the flow path 23B as illustrated in FIG. 7 to the second chamber 32. Increasing the flow rate of the purge gas to be supplied to the first chamber 30 from the flow path 23B as illustrated in FIG. 5 can reduce mutual diffusion of the sample gas and the purge gas in the first chamber 30. In addition, increasing the flow rate of the purge gas to be supplied from the flow path 23B as illustrated in FIG. 5 to the first chamber 30 can decrease the time taken for the sample gas to be supplied to the second chamber 32.

[Example Operation of Gas Detection System]

Figure 10:
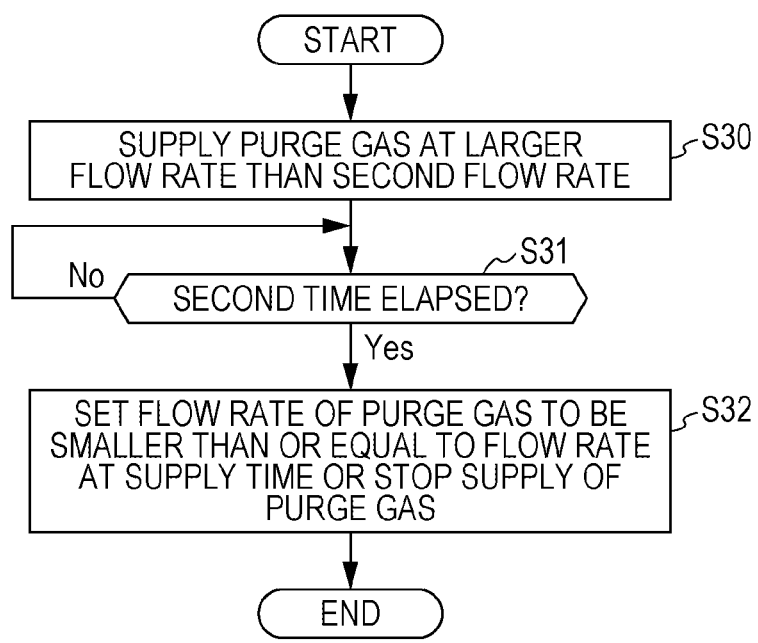
FIG. 10 is a flowchart illustrating the operation of the gas detection system illustrated in FIG. 1 during supply of a purge gas.

FIG. 10 is a flowchart illustrating the operation of the gas detection system 1 illustrated in FIG. 1. The control unit 64 may start a process as illustrated in FIG. 10 after a predetermined time elapses after it is detected that the subject has risen from the toilet seat 2B on the basis of the detection result of the sensor unit 63.

The control unit 64 performs control so that the purge gas is sucked in through the suction hole 21 (step S10). The control unit 64 performs control so that the purge gas from the suction hole 21 is stored in the fourth chamber 35 (step S11).

The control unit 64 performs control so that the sample gas is sucked in through the suction hole 20 after a predetermined time elapses after it is detected that the subject has sat on the toilet seat 2B on the basis of the detection result of the sensor unit 63 (step S12). The control unit 64 performs control so that the sample gas from the suction hole 20 is stored in the first chamber 30 (step S13) (see FIG. 4). The control unit 64 performs control so that the sample gas stored in the first chamber 30 is supplied to the second chamber 32 (step S14) (see FIG. 5).

The control unit 64 performs control so that the purge gas is supplied to the third chamber 33 via the fifth chamber 37 (step S15) (see FIG. 6). That is, in the processing of step S15, the control unit 64 performs control so that the purge gas is supplied to the sensor units 34. The details of the processing of step S15 will be described below with reference to FIG. 10.

The control unit 64 performs control so that the sample gas is supplied to the third chamber 33 (step S16) (see FIG. 7). That is, in the processing of step S16, the control unit 64 performs control so that the sample gas is supplied to the sensor units 34. The details of the processing of step S16 will be described below with reference to FIG. 11.

The control unit 64 alternately executes the processing of step S15 and the processing of step S16 a predetermined number of times, for example. The control unit 64 acquires voltage waveforms from the sensor units 34 (step S17).

The control unit 64 detects the type and concentration of gases contained in the sample gas by, for example, machine learning for the voltage waveforms acquired from the sensor units 34 (step S18). In the processing of step S18, the control unit 64 may transmit the detected type and concentration of the gases to the electronic device 3 via the communication unit 62 as a detection result.

As described above with reference to FIG. 8, the control unit 64 performs control so that the sample gas remaining in the first chamber 30 is discharged from the first chamber 30 (step S19).

After the processing of step S14 is completed, the control unit 64 may execute the processing of step S18 in parallel to the processing of step S15.

Figure 9:
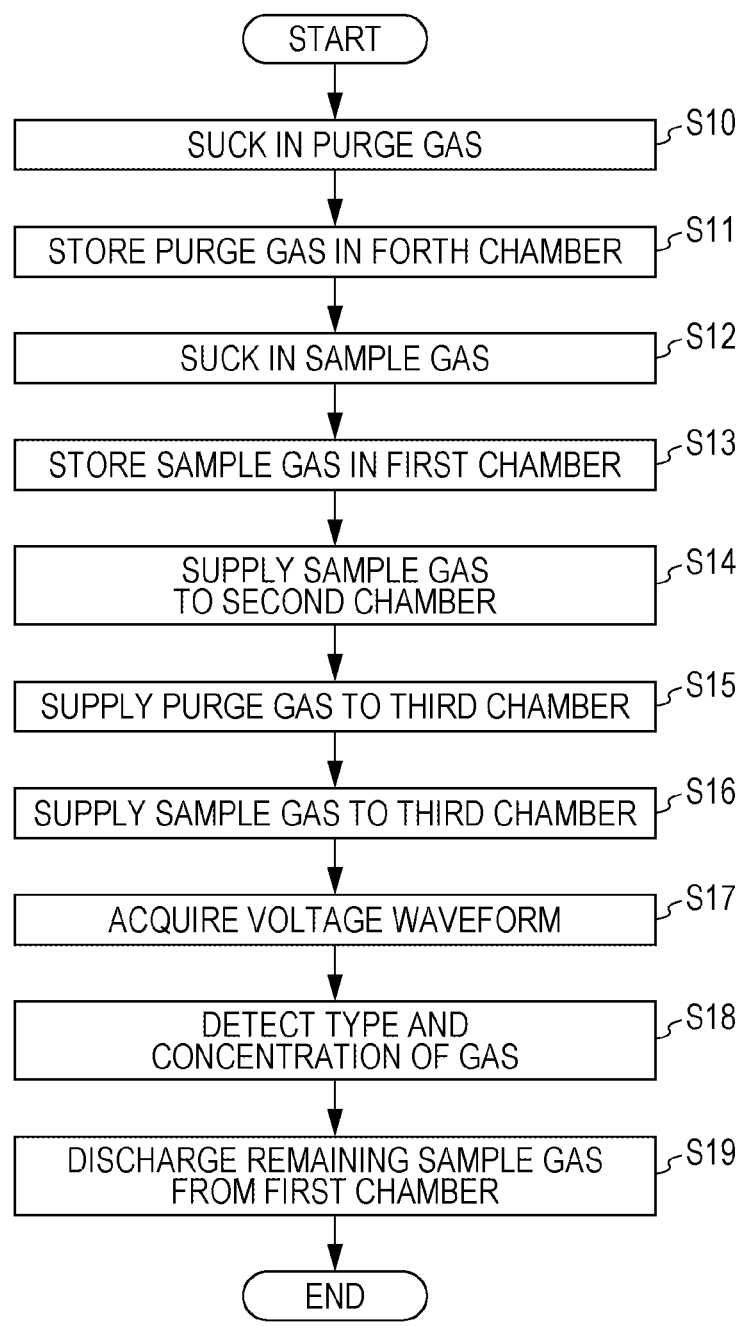
FIG. 9 is a flowchart illustrating the operation of the gas detection system illustrated in FIG. 1.

FIG. 10 is a flowchart illustrating the operation of the gas detection system 1 illustrated in FIG. 1 during supply of the purge gas. A process as illustrated in FIG. 10 corresponds to the details of the processing of step S15 as illustrated in FIG. 9. After executing the processing of step S14 as illustrated in FIG. 9, the control unit 64 may start the process as illustrated in FIG. 10.

The control unit 64 performs control so that the purge gas is supplied to the third chamber 33 at a flow rate larger than the second flow rate (step S30). In other words, the control unit 64 performs control so that the flow rate of the purge gas at the start of supply to the sensor units 34 is larger than the second flow rate.

The control unit 64 determines whether the second time has elapsed since the start of supply of the purge gas to the sensor units 34 (step S31). If the control unit 64 determines that the second time has elapsed since the start of supply of the purge gas to the sensor units 34 (step S31: Yes), the control unit 64 proceeds to the processing of step S32. On the other hand, if the control unit 64 determines that the second time has not elapsed since the start of supply of the purge gas to the sensor units 34 (step S31: No), the control unit 64 repeatedly executes the processing of step S31.

In the processing of step S32, the control unit 64 performs control so that the flow rate of the purge gas is smaller than or equal to the flow rate of the purge gas at the start of supply, or stops the supply of the purge gas to the sensor units 34.

Figure 11:
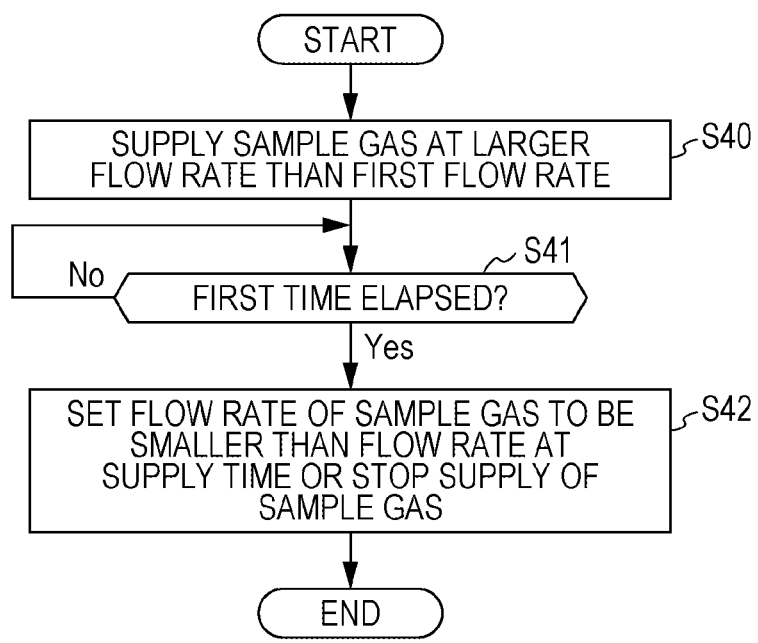
FIG. 11 is a flowchart illustrating the operation of the gas detection system illustrated in FIG. 1 during supply of a sample gas.

FIG. 11 is a flowchart illustrating the operation of the gas detection system 1 illustrated in FIG. 1 during the supply of the sample gas. A process as illustrated in FIG. 11 corresponds to the details of the processing of step S16 as illustrated in FIG. 9. After executing the processing of step S15 as illustrated in FIG. 9, the control unit 64 may start the process as illustrated in FIG. 11.

The control unit 64 performs control so that the sample gas is supplied to the third chamber 33 at a flow rate larger than the first flow rate (step S40). In other words, the control unit 64 performs control so that the flow rate of the sample gas at the start of supply to the sensor units 34 is larger than the first flow rate.

The control unit 64 determines whether the first time has elapsed since the start of supply of the sample gas to the sensor units 34 (step S41). If the control unit 64 determines that the first time has elapsed since the start of supply of the sample gas to the sensor units 34 (step S41: Yes), the control unit 64 proceeds to the processing of step S42. On the other hand, if the control unit 64 determines that the first time has not elapsed since the start of supply of the sample gas to the sensor units 34 (step S41: No), the control unit 64 repeatedly executes the processing of step S41.

In the processing of step S42, the control unit 64 performs control so that the flow rate of the sample gas is smaller than the flow rate of the sample gas at the start of supply, or stops the supply of the sample gas to the sensor units 34.

As described above, in the gas detection system 1 according to this embodiment, the second chamber 32 has a smaller area than the first chamber 30 in the cross section perpendicular to the gas flow direction in the first chamber 30. In the second chamber 32, the purge gas and the sample gas can be brought into contact with each other by the execution of, for example, the configuration as illustrated in FIG. 5 and the configuration as illustrated in FIG. 7. In this embodiment, making the second chamber 32 have a smaller area than the area of the first chamber 30 in the cross section perpendicular to the gas flow direction in the first chamber 30 can reduce the area of the boundary where the purge gas and the sample gas are in contact with each other. The reduced area of the boundary where the purge gas and the sample gas are in contact with each other can make it less likely that the purge gas and the sample gas are mixed in the second chamber 32. As described above, in this embodiment, making the second chamber 32 have a smaller cross-sectional area than the cross-sectional area of the first chamber 30 can make it less likely that the purge gas and the sample gas are mixed in the second chamber 32. In this embodiment, since the purge gas and the sample gas are less likely to be mixed, it is possible to more accurately detect the type and concentration of gases.

In the gas detection system 1 according to this embodiment, the control unit 64 performs control so that the flow rate of the sample gas, after the lapse of the first time from the start of supply of the sample gas to the sensor units 34, is smaller than the flow rate of the sample gas at the start of supply. Alternatively, the control unit 64 stops the supply of the sample gas to the sensor units 34 after the lapse of the first time described above. As described above, the sample gas is a gas generated from feces. Thus, the amount of sample gas that can be acquired may be limited. In particular, when the sample gas is concentrated, the amount of the sample gas is reduced. Even in this case, for example, the control unit 64 sets the flow rate of the sample gas after the lapse of the first time to be smaller than the flow rate of the sample gas at the start of supply. Thus, the control unit 64 can continuously supply the sample gas to the sensor units 34 for a longer period of time than when the flow rate of the sample gas is not reduced. With this configuration, the sensor units 34 can stably output voltages corresponding to specific gases contained in the sample gas. Since the sensor units 34 can stably output voltages, the gas detection system 1 can more accurately detect the type and concentration of gases. In addition, with this configuration, the gas detection system 1 can detect the type and concentration of gases even by using a small amount of sample gas. Thus, the device scale in the gas detection system 1 can be reduced. That is, it is possible to reduce the size of the gas detection system 1 while maintaining the detection accuracy.

According to this embodiment, therefore, the improved gas detection system 1 can be provided.

The drawings describing an embodiment according to the present disclosure are schematic ones. Dimensional ratios and the like in the drawings do not necessarily match the actual ones.

While an embodiment according to the present disclosure has been described with reference to the drawings and examples, it should be noted that various modifications or changes can be easily made by a person skilled in the art on the basis of the present disclosure. Accordingly, it should be noted that these modifications or changes fall within the scope of the present disclosure. For example, the functions and the lie included in each component or the like can be rearranged in any manner that is not logically contradictory, and a plurality of components or the like may be combined into one or divided.

Figure 12:
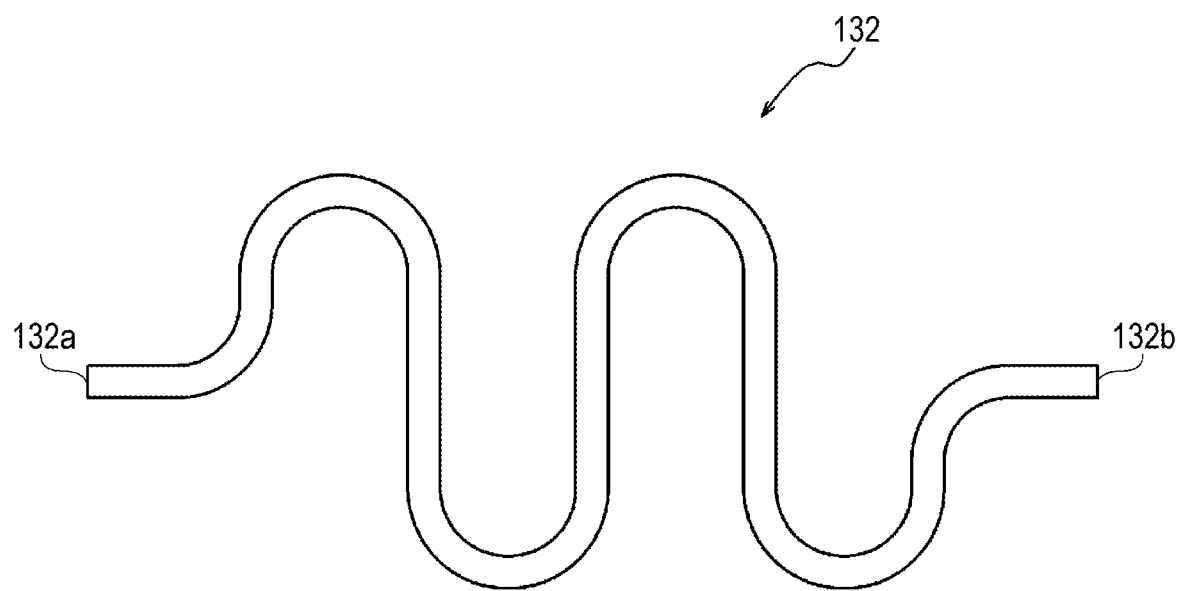
FIG. 12 is a diagram illustrating another example of a second chamber illustrated in FIG. 2.

For example, in the embodiment described above, as illustrated in FIG. 2, the second chamber 32 has been described as extending along a straight line. However, the second chamber according to the present disclosure is not limited to the one extending along a straight line. For example, the second chamber according to the present disclosure may have a shape as illustrated in FIG. 12. A second chamber 132 as illustrated in FIG. 12 has a curved portion. The shape of the curved portion is, for example, a meandering shape. The second chamber 132 includes an inlet 132a and an outlet 132b at both ends thereof. The inlet 132a is connectable to the outlet 30b of the first chamber 30 as illustrated in FIG. 2. The outlet 132b is connectable to the inlet 33a of the third chamber 33 as illustrated in FIG. 2. The second chamber 132 as illustrated in FIG. 12 has a smaller cross-sectional area than the first chamber 30 as illustrated in FIG. 2. Since the second chamber 132 as illustrated in FIG. 12 has a curved portion, and the curved portion has, for example, a meandering shape, the second chamber 132 can have a smaller cross-sectional area than the first chamber 30 while maintaining the volumetric capacity of the curved portion and the occupied volume of the second chamber 132.

For example, in the embodiment described above, the first chamber 30 as illustrated in FIG. 2 has been described as being configured to store a sample gas, as illustrated in FIG. 4. However, the uses of the first chamber 30 are not limited to this. The first chamber 30 may be used to concentrate the sample gas. In this case, the adsorbent 31 may adsorb a gas to be detected contained in the sample gas. Examples of the adsorbent 31 that adsorbs a gas to be detected include activated carbon and molecular sieve. However, the combination of them may be appropriately changed according to the polarity of gas molecules to be adsorbed. Further, the first chamber 30 may have a heater on the outside thereof.

For example, in the embodiment described above, the configuration of the gas detection system 1 has been described as the configuration as illustrated in FIG. 2. However, the configuration of the gas detection system 1 is not limited to the configuration as illustrated in FIG. 2. For example, the gas detection system 1 may adopt configurations as illustrated in FIGS. 13 to 17.

Figure 13:
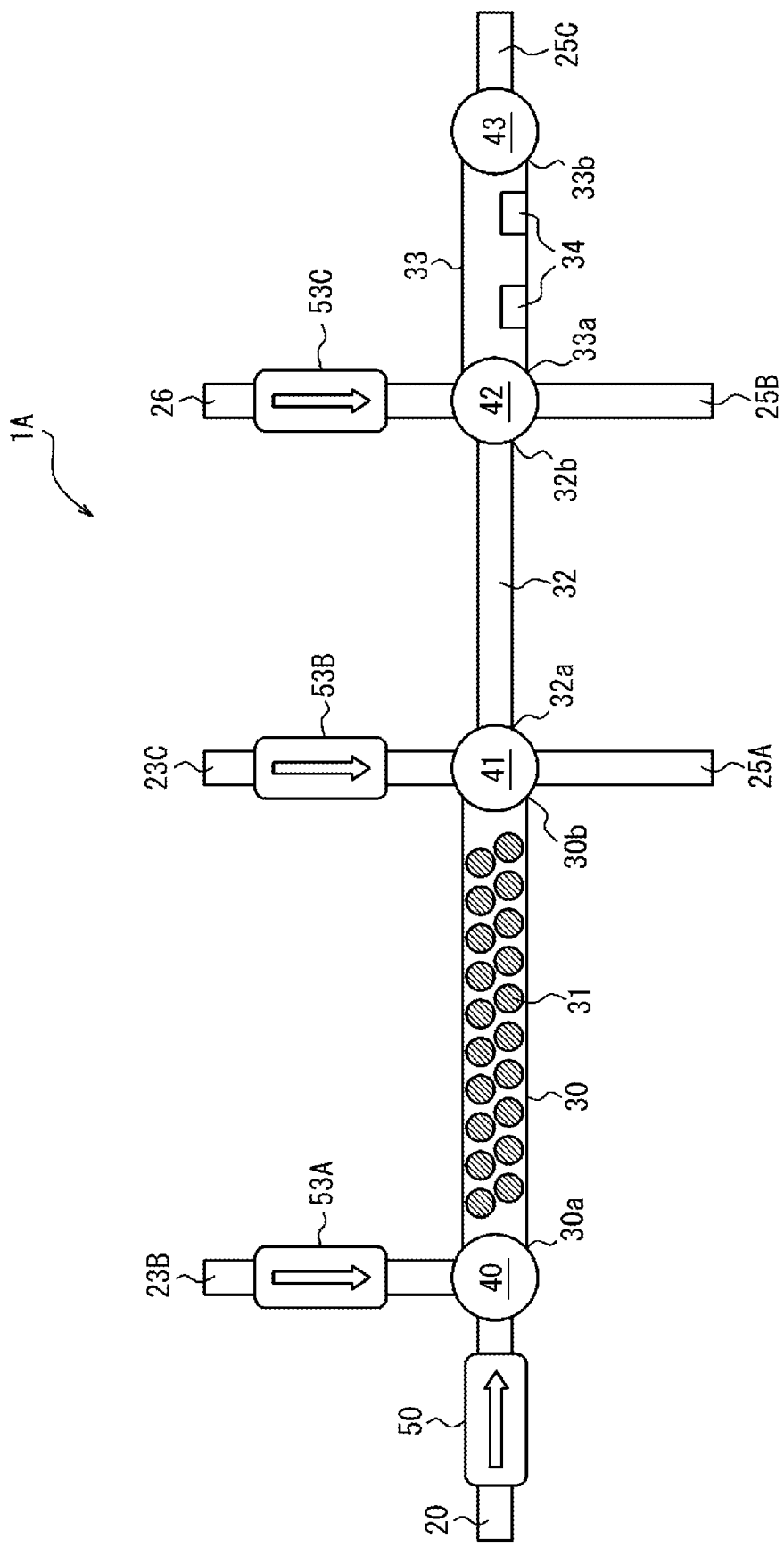
FIG. 13 is a diagram illustrating other example 1 of part of the configuration illustrated in FIG. 2.

A gas detection system 1A as illustrated in FIG. 13 includes a flow path 26 in place of the fourth chamber 35 and the fifth chamber 37 as illustrated in FIG. 2. The gas detection system 1A includes the supply unit 50 and supply units 53A, 53B, and 53C as supply units. The flow path 26 directly connects the suction hole 21 as illustrated in FIG. 2 and a connection port of the valve 42 to each other. The flow path 26 may be constituted by a tubular member such as a resin tube or a metal or glass pipe. The supply unit 53A is attached to the flow path 23B. The supply unit 53B is attached to the flow path 23C. The supply unit 53C is attached to the flow path 26. The respective arrows illustrated in the supply units 53A to 53C indicate the directions in which the supply units 53A to 53C send a gas. The supply units 53A to 53C may be each constituted by a piezoelectric pump, a motor pump, or the like.

In the configuration as illustrated in FIG. 13, the control unit 64 causes the valve 40 to connect the flow path 23B and the inlet 30a of the first chamber 30 to each other, and controls the supply unit 53A to supply the purge gas from the suction hole 21 as illustrated in FIG. 2 to the first chamber 30. Further, the control unit 64 causes the valve 41 to connect the flow path 23C and the inlet 32a of the second chamber 32 to each other, and controls the supply unit 53B to supply the purge gas from the suction hole 21 as illustrated in FIG. 2 to the second chamber 32. Further, the control unit 64 causes the valve 42 to connect the flow path 26 and the inlet 33a of the third chamber 33 to each other, and controls the supply unit 53C to supply the purge gas from the suction hole 21 as illustrated in FIG. 2 to the third chamber 33.

Figure 14:
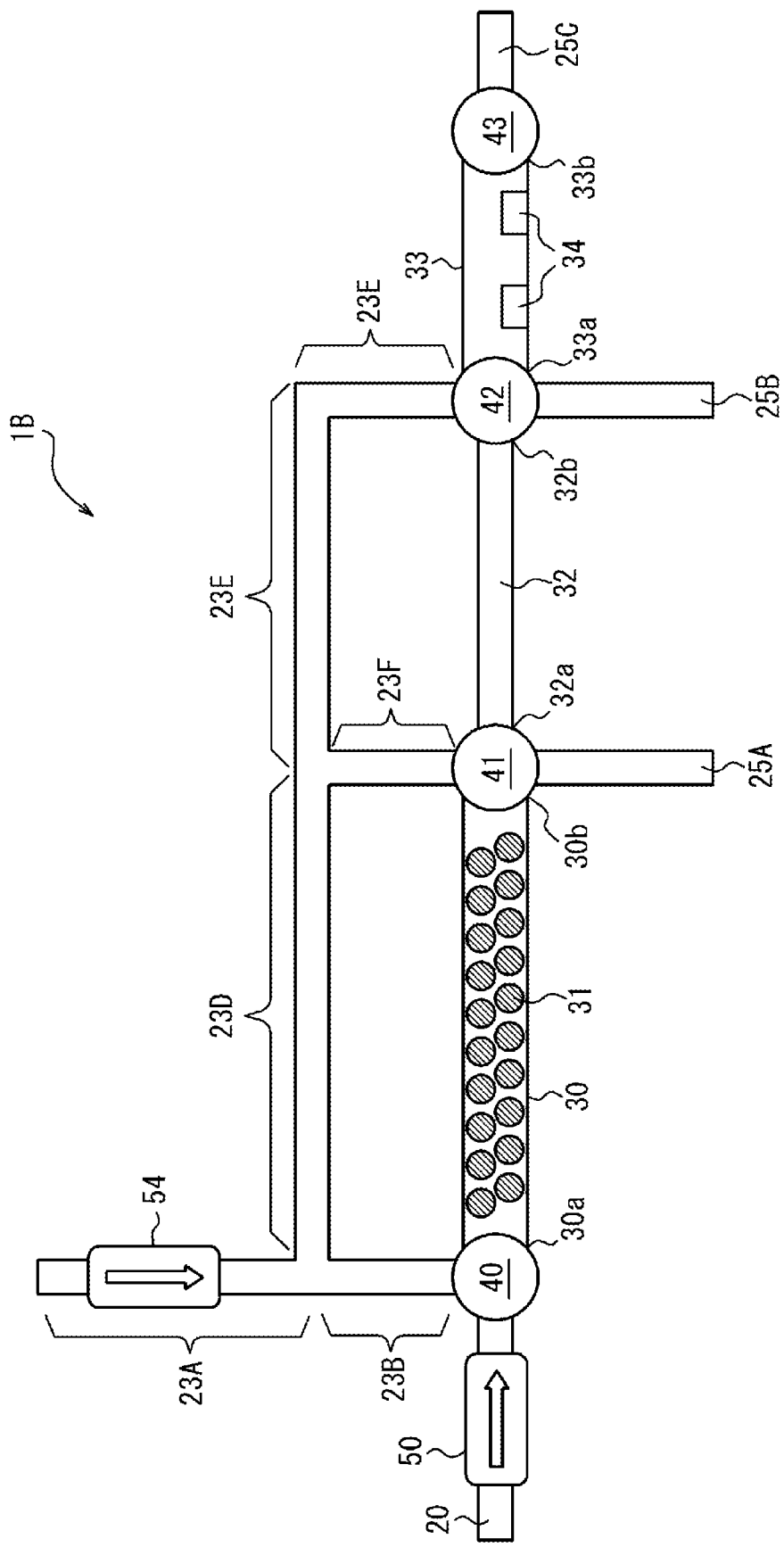
FIG. 14 is a diagram illustrating other example 2 of part of the configuration illustrated in FIG. 2.

A gas detection system 1B as illustrated in FIG. 14 includes flow paths 23D, 23E, and 23F in place of the flow path 23C, the fourth chamber 35, and the fifth chamber 37 as illustrated in FIG. 2. The gas detection system 1B includes the supply unit 50 and a supply unit 54 as supply units. One end of the flow path 23D is connected to one end of the flow path 23A and one end of the flow path 23B. The other end of the flow path 23D is connected to one end of the flow path 23E and one end of the flow path 23F. One end of the flow path 23E is connected to one end of the flow path 23D and one end of the flow path 23F. The other end of the flow path 23E is connected to a connection port of the valve 42. One end of the flow path 23F is connected to one end of the flow path 23D and one end of the flow path 23E. The other end of the flow path 23F is connected to a connection port of the valve 41. The flow paths 23D, 23E, and 23F may be each constituted by a tubular member such as a resin tube or a metal or glass pipe. The supply unit 54 is attached to the flow path 23A. The arrow illustrated in the supply unit 54 indicates the direction in which the supply unit 54 sends a gas. The supply unit 54 may be constituted by a piezoelectric pump or the like.

In the configuration as illustrated in FIG. 14, the control unit 64 causes the valve 40 to connect the flow path 23B and the inlet 30a of the first chamber 30 to each other, and controls the supply unit 54 to supply the purge gas from the suction hole 21 as illustrated in FIG. 2 to the first chamber 30. Further, the control unit 64 causes the valve 41 to connect the flow path 23F and the inlet 32a of the second chamber 32 to each other, and controls the supply unit 54 to supply the purge gas from the suction hole 21 as illustrated in FIG. 2 to the second chamber 32. Further, the control unit 64 causes the valve 42 to connect the flow path 23E and the inlet 33a of the third chamber 33 to each other, and controls the supply unit 54 to supply the purge gas from the suction hole 21 as illustrated in FIG. 2 to the third chamber 33.

Figure 15:
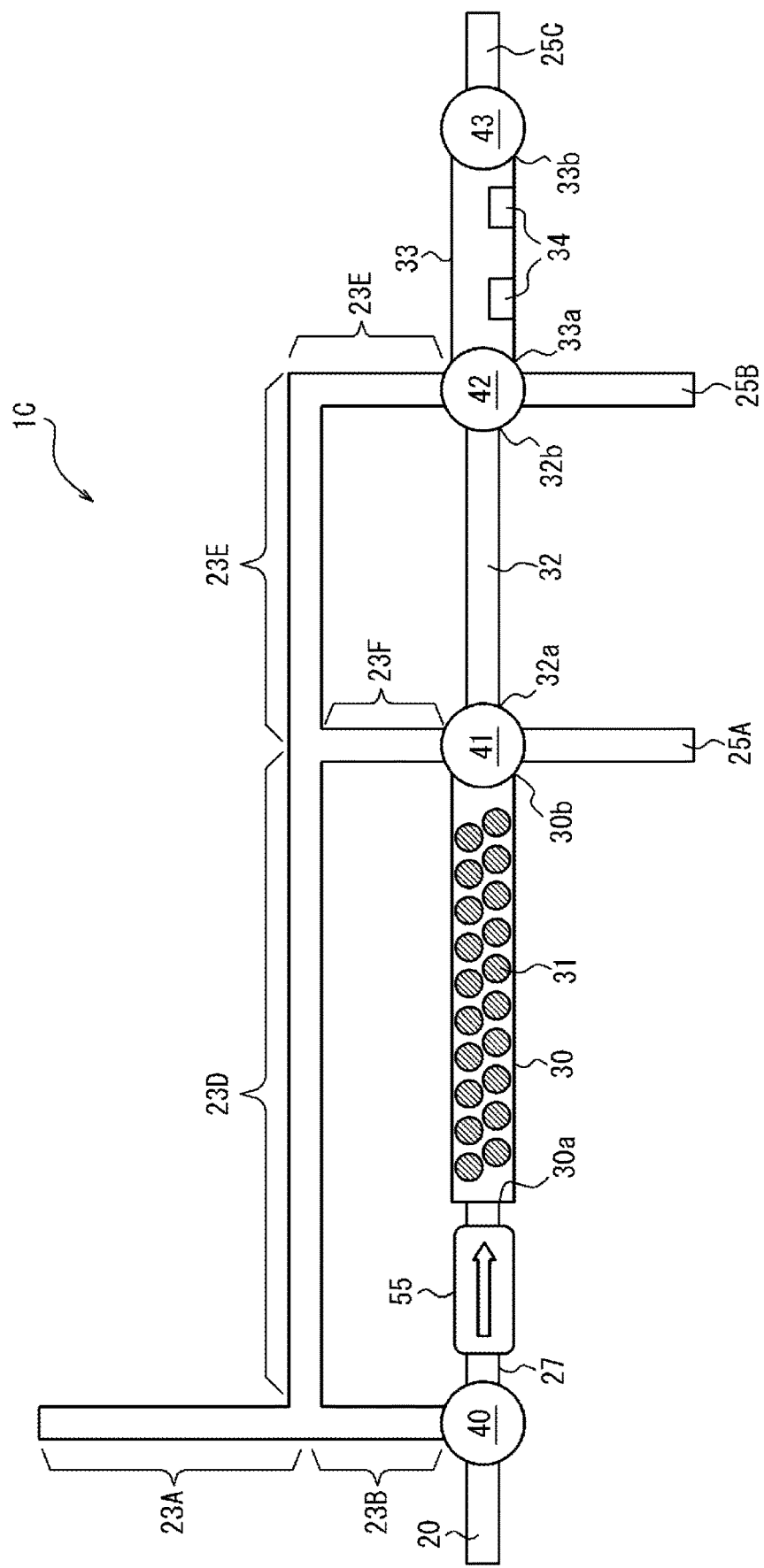
FIG. 15 is a diagram illustrating other example 3 of part of the configuration illustrated in FIG. 2.

A gas detection system 1C as illustrated in FIG. 15 includes flow paths 23D, 23E, and 23F, as in the configuration as illustrated in FIG. 14. The gas detection system 1 includes a flow path 27. The gas detection system 1C includes a supply unit 55 as a supply unit. One end of the flow path 27 is connected to a connection port of the valve 40. The other end of the flow path 27 is connected to the inlet 30a of the first chamber 30. The flow path 27 may be constituted by a tubular member such as a resin tube or a metal or glass pipe. The supply unit 55 is attached to the flow path 27. The arrow illustrated in the supply unit 55 indicates the direction in which the supply unit 55 sends a gas. The supply unit 55 may be constituted by a piezoelectric pump, a motor pump, or the like.

Figure 16:
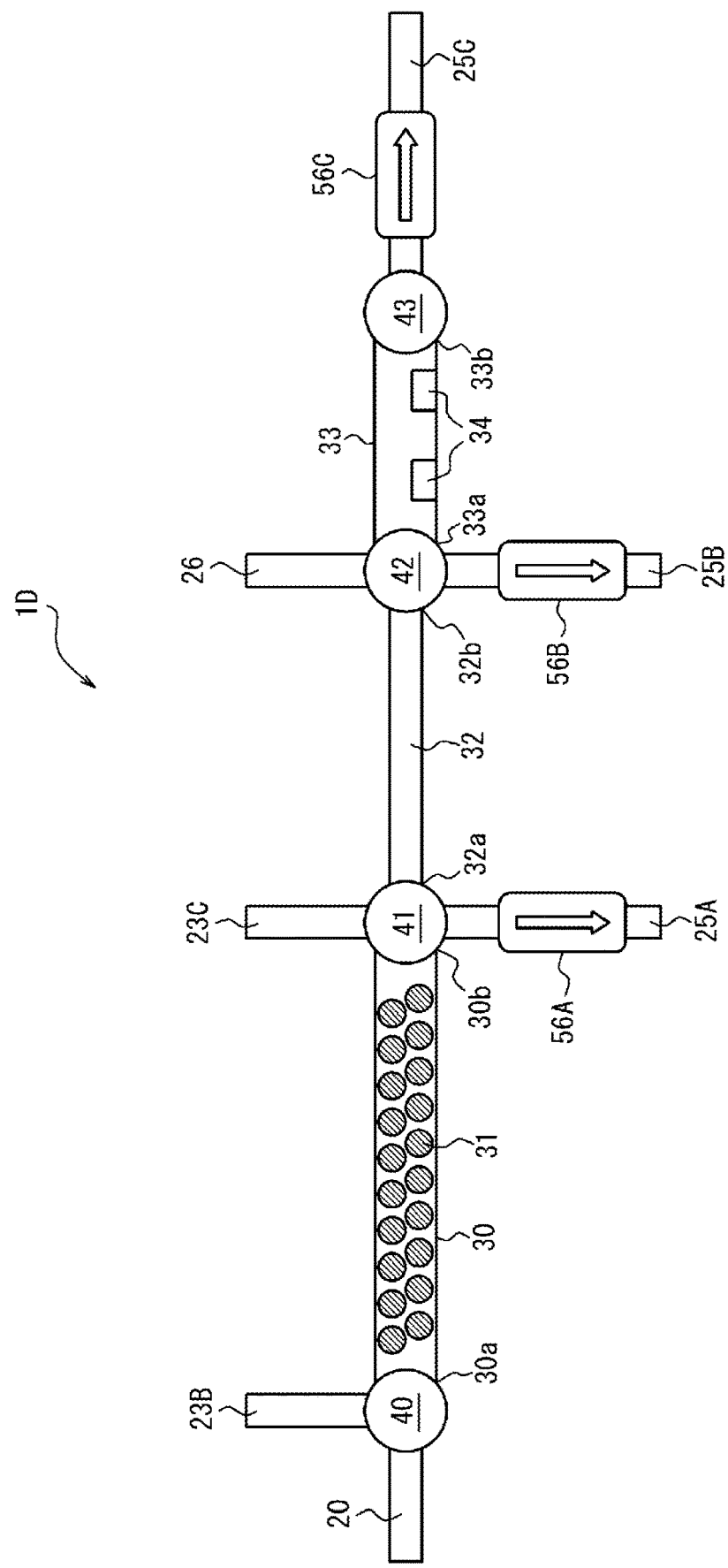
FIG. 16 is a diagram illustrating other example 4 of part of the configuration illustrated in FIG. 2.

A gas detection system 1D as illustrated in FIG. 16 includes the flow path 26, as in the configuration as illustrated in FIG. 13. The gas detection system 1D includes supply units 56A, 56B, and 56C as supply units.

The supply unit 56A is attached to the flow path 25A. The supply unit 56B is attached to the flow path 25B. The supply unit 56C is attached to the flow path 25C. The respective arrows illustrated in the supply units 56A to 56C indicate the directions in which the supply units 56A to 56C send a gas. The supply units 56A to 56C may be each constituted by a piezoelectric pump, a motor pump, or the like.

In the configuration as illustrated in FIG. 16, the control unit 64 causes the valve 40 to connect the suction hole 20 and the inlet 30a of the first chamber 30 to each other, and causes the valve 41 to connect the outlet 30b of the first chamber 30 and the flow path 25A to each other. Further, the control unit 64 controls the supply unit 56A to supply the sample gas from the suction hole 20 to the first chamber 30.

In the configuration as illustrated in FIG. 16, the control unit 64 causes the valve 40 to connect the suction hole 20 and the inlet 30a of the first chamber 30 to each other, and causes the valve 41 to connect the outlet 30b of the first chamber 30 and the inlet 32a of the second chamber 32 to each other. Further, the control unit 64 causes the valve 42 to connect the outlet 32b of the second chamber 32 and the flow path 25B to each other. In addition, the control unit 64 controls the supply unit 56B to supply the purge gas from the suction hole 21 as illustrated in FIG. 2 to the first chamber 30 via the flow path 23B. The purge gas supplied to the first chamber 30 pushes out the sample gas in the first chamber 30 to the second chamber 32. With this configuration, the sample gas in the first chamber 30 is supplied to the second chamber 32.

In the configuration as illustrated in FIG. 16, the control unit 64 causes the valve 41 to connect the flow path 23C and the inlet 32a of the second chamber 32 to each other, and causes the valve 42 to connect the outlet 32b of the second chamber 32 and the inlet 33a of the third chamber 33 to each other. Further, the control unit 64 causes the valve 43 to connect the outlet 33b of the third chamber 33 and the flow path 25C to each other. In addition, the control unit 64 controls the supply unit 56C to supply the purge gas from the suction hole 21 as illustrated in FIG. 2 to the second chamber 32 via the flow path 23C. The purge gas supplied from the flow path 23C to the second chamber 32 pushes out the sample gas in the second chamber 32 to the third chamber 33. With this configuration, the sample gas in the second chamber 32 is supplied to the third chamber 33 and supplied to the sensor units 34.

In the configuration as illustrated in FIG. 16, the control unit 64 causes the valve 42 to connect the flow path 26 and the inlet 33a of the third chamber 33 to each other, and causes the valve 43 to connect the outlet 33b of the third chamber 33 and the flow path 25C to each other. Further, the control unit 64 controls the supply unit 56C to supply the purge gas from the suction hole 21 as illustrated in FIG. 2 to the third chamber 33 via the flow path 26.

Figure 17:
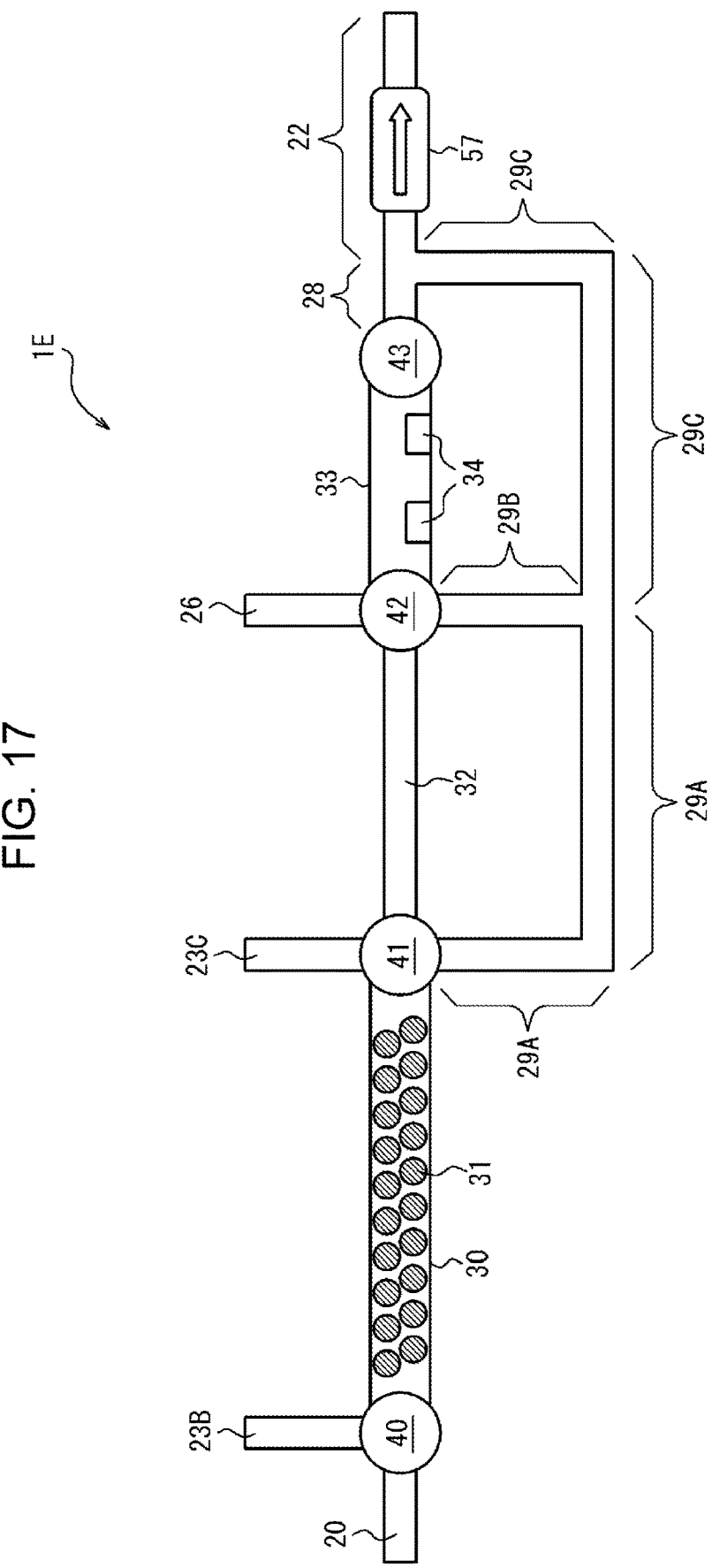
FIG. 17 is a diagram illustrating other example 5 of part of the configuration illustrated in FIG. 2.

A gas detection system 1E as illustrated in FIG. 17 includes the flow path 26, as in the configuration as illustrated in FIG. 13. The gas detection system 1E includes flow paths 28, 29A, 29B, and 29C in place of the flow paths 25A, 25B, 25C, 25E, and 25F as illustrated in FIG. 2. The gas detection system 1E includes a supply unit 57 as a supply unit. One end of the flow path 28 is connected to a connection port of the valve 43. The other end of the flow path 28 is connected to the discharge path 22. One end of the flow path 29A is connected to a connection port of the valve 41. The other end of the flow path 29A is connected to one end of the flow path 29B and one end of the flow path 29C. One end of the flow path 29B is connected to a connection port of the valve 42. The other end of the flow path 29B is connected to one end of the flow path 29A and one end of the flow path 29C. The other end of the flow path 29C is connected to one end of the flow path 28 and the discharge path 22. The other end of the flow path 29C is connected to one end of the flow path 29A and one end of the flow path 29B. The flow paths 28 and 29A to 29C may be each constituted by a tubular member such as a resin tube or a metal or glass pipe. The supply unit 57 is attached to the discharge path 22. The arrow illustrated in the supply unit 57 indicates the direction in which the supply unit 57 sends a gas. The supply unit 57 may be constituted by a piezoelectric pump, a motor pump, or the like.

For example, in the embodiment described above, as illustrated in FIG. 4, the gas detection system 1 has been described as a single device. However, the gas detection system according to the present disclosure is not limited to the single device. The gas detection system according to the present disclosure may include a plurality of independent devices. The gas detection system according to the present disclosure may have, for example, a configuration as illustrated in FIG. 18.

A gas detection system 1F as illustrated in FIG. 18 includes a gas detection device 4 and a server device 5.

The gas detection device 4 and the server device 5 are capable of communicating with each other via a network 6. A portion of the network 6 may be wired or wireless. The gas detection device 4 has a configuration similar to the configuration of the gas detection system 1 as illustrated in FIG. 2. The server device 5 includes a storage unit 5A, a communication unit 5B, and a control unit 5C. The control unit 5C is capable of executing the processes of the control unit 64 as illustrated in FIG. 4 described above. For example, the control unit 5C is capable of controlling flow rates of a sample gas and a purge gas to be supplied to the sensor units 34 as illustrated in FIG. 2. When supplying a sample gas to the sensor units 34, the control unit 5C performs control so that the flow rate of the sample gas, after the lapse of the first time from the start of supply of the sample gas to the sensor units 34, is smaller than the flow rate of the sample gas at the start of supply. Alternatively, the control unit 5C stops the supply of the sample gas to the sensor units 34 after the lapse of the first time described above. Further, for example, when supplying a purge gas to the sensor units 34, the control unit 5C performs control so that the flow rate of the purge gas, after the lapse of the second time from the start of supply of the purge gas to the sensor units 34, is smaller than or equal to the flow rate of the purge gas at the start of supply. Alternatively, the control unit 5C stops the supply of the purge gas to the sensor units 34 after the lapse of the second time described above.

In the present disclosure, descriptions such as "first" and "second" are identifiers for distinguishing the respective configurations. The configurations distinguished by the descriptions such as "first" and "second" in the present disclosure may be interchangeably numbered. For example, a first terminal and a second terminal may exchange their identifiers "first" and "second". The identifiers are exchanged simultaneously. Even after the identifiers are exchanged, the respective configurations are distinguishable. The identifiers may be deleted. Configurations without identifiers are distinguished using reference numerals. Only the description of identifiers such as "first" and "second" in the present disclosure should not be used for interpreting the order of the configurations or as a basis of the presence of identifiers with smaller numbers.

REFERENCE SIGNS LIST 1, 1A to 1F gas detection system
2 toilet
2A toilet bowl
2B toilet seat
3 electronic device
3A display unit
4 gas detection device
5 server device
5A storage unit
5B communication unit
5C control unit
6 network
10 housing
20, 21 suction hole
20A, 21A air blower
22 discharge path
23A to 23F, 24A to 24D, 25A to 25F, 26 to 28, 29A, 29B flow path
30 first chamber
31 adsorbent
32, 132 second chamber
33 third chamber
34 sensor unit
35 fourth chamber
36 adsorbent
37 fifth chamber
30a , 32a , 33a , 35a , 37a , 132a inlet
30b , 32b , 33b , 35b , 37b , 132b outlet
40 to 45 valve
50 to 52, 53A to 53C, 54, 55, 56A to 56C, 57 supply unit
60 circuit board
61 storage unit
62 communication unit
63 sensor unit
64 control unit

The invention claimed is:

1. A gas detection system comprising:
a first sensor unit that outputs a voltage corresponding to a concentration of a specific gas;
a chamber capable of storing a sample gas; and
a control unit capable of controlling flow rates of the sample gas and a purge gas that are supplied to the first sensor unit, wherein
when supplying the sample gas to the first sensor unit, the control unit performs control so that a flow rate of the sample gas, after a lapse of a first time from a start of supply of the sample gas to the sensor unit, is smaller than a flow rate of the sample gas at the start of supply, the first time is set based on the amount of sample gas that can be stored in the chamber.

2. The gas detection system according to claim 1, wherein the control unit is configured to store the sample gas in a chamber and is further configured to supply the sample gas stored in the chamber to the first sensor unit.

3. The gas detection system according to claim 2, further comprising a second sensor unit capable of detecting that a subject has sat on a toilet seat, wherein the control unit performs control so that the sample gas is stored in the chamber after a predetermined time elapses after the second sensor unit detected that the subject has sat on the toilet seat.

4. The gas detection system according to claim 1, wherein the control unit starts supplying the purge gas to the first sensor unit after a lapse of a second time from a start of supply of the purge gas to the first sensor unit, wherein the second time is longer than the first time.

5. The gas detection system according to claim 1, wherein when supplying the purge gas to the first sensor unit, the control unit performs control so that a flow rate of the purge gas, after a lapse of a second time from a start of supply of the purge gas to the first sensor unit, is smaller than or equal to a flow rate of the purge gas at the start of supply.

6. The gas detection system according to claim 5, wherein the control unit alternately supplies the purge gas and the sample gas to the first sensor unit.

7. The gas detection system according to claim 1, wherein when supplying the purge gas to the first sensor unit, after a lapse of a second time from a start of supply of the purge gas to the first sensor unit, the control unit stops the supply of the purge gas to the first sensor unit.

8. The gas detection system according to claim 1, wherein the control unit performs control so that the flow rate of the purge gas to be supplied to the first sensor unit is larger than the flow rate of the sample gas to be supplied to the first sensor unit.

* * * * *